(12) United States Patent
Muller-Cohn et al.

(10) Patent No.: US 8,900,856 B2
(45) Date of Patent: Dec. 2, 2014

(54) INTEGRATION OF SAMPLE STORAGE AND SAMPLE MANAGEMENT FOR LIFE SCIENCE

(75) Inventors: Judy Muller-Cohn, Del Mar, CA (US); Rolf Muller, Del Mar, CA (US); Corinna Herrnstadt, San Diego, CA (US)

(73) Assignee: Biomatrica, Inc., San Diego, CA (US)

( * ) Notice: Subject to any disclaimer, the term of this patent is extended or adjusted under 35 U.S.C. 154(b) by 1658 days.

(21) Appl. No.: 11/102,588

(22) Filed: Apr. 8, 2005

(65) Prior Publication Data
US 2005/0276728 A1 Dec. 15, 2005

Related U.S. Application Data

(60) Provisional application No. 60/560,829, filed on Apr. 8, 2004.

(51) Int. Cl.
| | | |
|---|---|---|
| *C12M 1/00* | (2006.01) | |
| *C12M 3/00* | (2006.01) | |
| *A01N 1/02* | (2006.01) | |
| *B01L 3/00* | (2006.01) | |
| *A01N 1/00* | (2006.01) | |
| *B82Y 30/00* | (2011.01) | |
| *G01N 35/00* | (2006.01) | |
| *G01N 35/02* | (2006.01) | |

(52) U.S. Cl.
CPC .. *A01N 1/00* (2013.01); *A01N 1/02* (2013.01); *B01L 3/50255* (2013.01); *G01N 2035/00782* (2013.01); *B01L 3/545* (2013.01); *B01L 2400/0487* (2013.01); *G01N 2035/00108* (2013.01); *B01L 3/50853* (2013.01); *B82Y 30/00* (2013.01); *B01L 2300/069* (2013.01); *B01L 3/5085* (2013.01); *G01N 35/00871* (2013.01); *A01N 1/0263* (2013.01); *B01L 2300/023* (2013.01); *G01N 35/028* (2013.01); *B01L 3/50855* (2013.01); *B01L 2300/022* (2013.01); *B01L 2300/0829* (2013.01); *B01L 2300/043* (2013.01)

USPC ........... 435/307.1; 435/287.1

(58) Field of Classification Search
CPC ..... A01N 1/02; A01N 1/0263; A01N 1/0257; A61B 10/0096; C12M 45/22; G01N 33/54366; G01N 33/54373; B01J 2219/00722; B01J 19/0046; B82Y 30/00
USPC ............. 435/307.1, 287.1; 422/6
See application file for complete search history.

(56) References Cited

U.S. PATENT DOCUMENTS

| | | | |
|---|---|---|---|
| 4,024,548 A | 5/1977 | Alonso et al. | 346/140 R |
| 4,127,502 A | 11/1978 | Li Mutti et al. | |

(Continued)

FOREIGN PATENT DOCUMENTS

| | | |
|---|---|---|
| CA | 1022441 | 12/1977 |
| CA | 2467563 A1 | 5/2003 |

(Continued)

OTHER PUBLICATIONS

Boyd et al., "Stabilization effect of polyvinyl alcohol on horseradish peroxidase, glucose oxidase, β-galatosidase and alkaline phosphatase," Biotechnology Techniques 10(9):693-698, Sep. 1996.

(Continued)

*Primary Examiner* — Michael Hobbs
(74) *Attorney, Agent, or Firm* — Wilson Sonsini Goodrich & Rosati

(57) ABSTRACT

Compositions and methods are disclosed for automated storing, tracking, retrieving and analyzing biological samples, including dry storage at ambient temperatures of nucleic acids, proteins (including enzymes), and cells using a dry storage matrix that permits recovery of biologically active materials. RFID-tagged biological sample storage devices featuring dissolvable or dissociable matrices are described for use as supports of biological samples, which matrices can be dried and subsequently rehydrated for sample recovery. Also disclosed are computer-implemented systems and methods for managing sample data.

12 Claims, 18 Drawing Sheets

(56) References Cited

U.S. PATENT DOCUMENTS

| | | | |
|---|---|---|---|
| 4,257,958 A | 3/1981 | Powell | |
| 4,264,560 A | 4/1981 | Natelson | |
| 4,451,569 A | 5/1984 | Kobayashi et al. | 435/188 |
| 4,806,343 A | 2/1989 | Carpenter et al. | 424/450 |
| 4,842,758 A | 6/1989 | Crutzen | |
| 4,889,818 A | 12/1989 | Gelfand et al. | |
| 4,891,319 A | 1/1990 | Roser | 435/188 |
| 4,898,813 A * | 2/1990 | Albarella et al. | 435/4 |
| 4,965,188 A | 10/1990 | Mullis et al. | |
| 5,039,704 A | 8/1991 | Smith et al. | |
| 5,047,342 A | 9/1991 | Chatterjee | |
| 5,078,997 A | 1/1992 | Hora et al. | |
| 5,079,352 A | 1/1992 | Gelfand et al. | |
| 5,089,407 A | 2/1992 | Baker et al. | 435/179 |
| 5,096,670 A | 3/1992 | Harris et al. | 422/65 |
| 5,098,893 A | 3/1992 | Franks et al. | |
| 5,198,353 A | 3/1993 | Hawkins et al. | |
| 5,200,399 A | 4/1993 | Wettlaufer et al. | |
| 5,240,843 A | 8/1993 | Gibson et al. | 435/188 |
| 5,270,179 A | 12/1993 | Chatterjee | |
| 5,290,765 A | 3/1994 | Wettlaufer et al. | |
| 5,315,505 A | 5/1994 | Pratt et al. | 364/413.01 |
| 5,351,801 A | 10/1994 | Markin et al. | 198/346.1 |
| 5,374,553 A | 12/1994 | Gelfand et al. | |
| 5,397,711 A | 3/1995 | Finckh | |
| 5,403,706 A | 4/1995 | Wilk et al. | |
| 5,418,141 A | 5/1995 | Zweig et al. | |
| 5,428,063 A | 6/1995 | Barak et al. | |
| 5,436,149 A | 7/1995 | Barnes | |
| 5,496,562 A | 3/1996 | Burgoyne | 424/488 |
| 5,512,462 A | 4/1996 | Cheng | |
| 5,516,644 A * | 5/1996 | Yamauchi et al. | 435/7.9 |
| 5,529,166 A | 6/1996 | Markin et al. | 198/349 |
| 5,556,771 A | 9/1996 | Shen et al. | 435/91.2 |
| 5,593,824 A | 1/1997 | Treml et al. | |
| 5,614,365 A | 3/1997 | Tabor et al. | |
| 5,684,045 A | 11/1997 | Smith et al. | |
| 5,705,366 A | 1/1998 | Backus | |
| 5,741,462 A | 4/1998 | Nova et al. | 422/68.1 |
| 5,751,629 A | 5/1998 | Nova et al. | 365/151 |
| 5,763,157 A | 6/1998 | Treml et al. | |
| 5,777,303 A | 7/1998 | Berney | 235/375 |
| 5,789,172 A | 8/1998 | Still et al. | |
| 5,798,035 A | 8/1998 | Kirk et al. | |
| 5,827,874 A | 10/1998 | Meyer et al. | |
| 5,834,254 A | 11/1998 | Shen et al. | 435/91.2 |
| 5,837,546 A | 11/1998 | Allen et al. | 436/169 |
| 5,856,102 A | 1/1999 | Bierke-Nelson et al. | 435/6 |
| 5,874,214 A | 2/1999 | Nova et al. | 435/6 |
| 5,876,992 A | 3/1999 | De Rosier et al. | 435/188 |
| 5,918,273 A | 6/1999 | Horn | 73/61.55 |
| 5,939,259 A | 8/1999 | Harvey et al. | |
| 5,945,515 A | 8/1999 | Chomczynski | |
| 5,955,448 A | 9/1999 | Colaco et al. | |
| 5,985,214 A | 11/1999 | Stylli et al. | |
| 5,991,729 A | 11/1999 | Barry et al. | 705/3 |
| 6,013,488 A | 1/2000 | Hayashizaki | |
| 6,017,496 A | 1/2000 | Nova et al. | 422/68.1 |
| 6,025,129 A | 2/2000 | Nova et al. | 435/6 |
| 6,037,168 A * | 3/2000 | Brown | 435/288.3 |
| 6,057,159 A | 5/2000 | Lepre | |
| 6,071,428 A | 6/2000 | Franks et al. | |
| 6,090,925 A * | 7/2000 | Woiszwillo et al. | 530/410 |
| 6,143,817 A | 11/2000 | Hallam et al. | |
| 6,156,345 A * | 12/2000 | Chudzik et al. | 424/484 |
| 6,166,117 A | 12/2000 | Miyazaki | |
| 6,168,922 B1 | 1/2001 | Harvey et al. | |
| 6,197,229 B1 | 3/2001 | Ando et al. | |
| 6,204,375 B1 | 3/2001 | Lader | |
| 6,221,599 B1 | 4/2001 | Hayashizaki | |
| 6,251,599 B1 | 6/2001 | Chen et al. | 435/6 |
| 6,284,459 B1 | 9/2001 | Nova et al. | 435/6 |
| 6,294,203 B1 | 9/2001 | Burgoyne | 424/488 |
| 6,294,338 B1 | 9/2001 | Nunomura | 435/6 |
| 6,313,102 B1 | 11/2001 | Colaco et al. | |
| 6,322,983 B1 | 11/2001 | Burgoyne | |
| 6,323,039 B1 | 11/2001 | Dykens et al. | |
| 6,329,139 B1 | 12/2001 | Nova et al. | 435/6 |
| 6,331,273 B1 | 12/2001 | Nova et al. | 422/68.1 |
| 6,352,854 B1 | 3/2002 | Nova et al. | 435/287.1 |
| 6,366,440 B1 * | 4/2002 | Kung | 361/147 |
| 6,372,428 B1 | 4/2002 | Nova et al. | 435/6 |
| 6,372,437 B2 | 4/2002 | Hayashizaki | |
| 6,380,858 B1 | 4/2002 | Yarin et al. | 340/573.1 |
| 6,416,714 B1 | 7/2002 | Nova et al. | 422/68.1 |
| 6,426,210 B1 | 7/2002 | Franks et al. | 435/260 |
| 6,447,726 B1 * | 9/2002 | Delucas et al. | 422/99 |
| 6,447,804 B1 | 9/2002 | Burgoyne | |
| RE37,872 E | 10/2002 | Franks et al. | |
| 6,458,556 B1 | 10/2002 | Hayashizaki | |
| 6,475,716 B1 | 11/2002 | Seki | |
| 6,503,411 B1 | 1/2003 | Franks et al. | |
| 6,503,702 B1 * | 1/2003 | Stewart | 435/5 |
| 6,528,309 B2 | 3/2003 | Levine | |
| 6,534,483 B1 | 3/2003 | Bruno et al. | 514/44 |
| 6,535,129 B1 | 3/2003 | Petrick | 340/572.1 |
| 6,602,718 B1 | 8/2003 | Augello et al. | |
| 6,610,531 B1 | 8/2003 | Mateczun et al. | 435/260 |
| 6,617,170 B2 | 9/2003 | Augello et al. | |
| 6,627,226 B2 | 9/2003 | Burgoyne et al. | 424/488 |
| 6,627,398 B1 | 9/2003 | Wilusz et al. | |
| 6,645,717 B1 | 11/2003 | Smith et al. | 435/6 |
| 6,649,406 B1 | 11/2003 | Williams et al. | |
| 6,653,062 B1 | 11/2003 | DePablo et al. | |
| 6,664,099 B1 | 12/2003 | Worall | |
| 6,667,167 B1 | 12/2003 | Sorensen et al. | 435/188 |
| 6,682,730 B2 * | 1/2004 | Mickle et al. | 424/93.21 |
| 6,689,353 B1 | 2/2004 | Wang et al. | |
| 6,696,028 B2 | 2/2004 | Bara | 422/299 |
| 6,746,841 B1 | 6/2004 | Fomovskaia et al. | |
| 6,746,851 B1 | 6/2004 | Tseung et al. | |
| 6,750,059 B1 | 6/2004 | Blakesley et al. | 435/471 |
| 6,776,959 B1 | 8/2004 | Helftenbein | |
| 6,787,305 B1 | 9/2004 | Li et al. | |
| 6,803,200 B2 | 10/2004 | Xia et al. | |
| 6,821,479 B1 | 11/2004 | Smith et al. | 422/1 |
| 6,821,789 B2 | 11/2004 | Augello et al. | |
| 6,858,634 B2 | 2/2005 | Asrar et al. | 514/372 |
| 6,861,213 B2 | 3/2005 | Oelmuller et al. | |
| 6,862,789 B1 | 3/2005 | Hering et al. | |
| 6,872,357 B1 * | 3/2005 | Bronshtein et al. | 422/41 |
| 6,896,894 B2 | 5/2005 | Brody et al. | |
| 6,919,172 B2 | 7/2005 | DePablo et al. | |
| 6,942,964 B1 | 9/2005 | Ward et al. | |
| 7,011,825 B2 | 3/2006 | Yamazaki et al. | |
| 7,049,065 B2 | 5/2006 | Hayashizaki | |
| 7,083,106 B2 | 8/2006 | Albany | 235/492 |
| 7,098,033 B2 | 8/2006 | Chen et al. | |
| 7,101,693 B2 | 9/2006 | Cicerone et al. | |
| 7,142,987 B2 | 11/2006 | Eggers | |
| 7,150,980 B1 | 12/2006 | Lapidot et al. | |
| 7,169,584 B2 | 1/2007 | Ward et al. | |
| RE39,497 E | 2/2007 | Franks et al. | |
| 7,172,999 B2 | 2/2007 | Mattern et al. | |
| 7,258,873 B2 | 8/2007 | Truong-Le et al. | |
| 7,270,953 B2 | 9/2007 | Hollander et al. | |
| 7,282,371 B2 | 10/2007 | Helftenbein | |
| 7,384,603 B2 | 6/2008 | Klein et al. | 422/68.1 |
| RE43,389 E | 5/2012 | Helftenbein | |
| 8,519,125 B2 | 8/2013 | Whitney | |
| 2001/0038858 A1 | 11/2001 | Roser et al. | |
| 2002/0039771 A1 | 4/2002 | Peters et al. | |
| 2002/0055118 A1 | 5/2002 | Eym | 435/6 |
| 2002/0076819 A1 | 6/2002 | Bowman et al. | 436/56 |
| 2002/0081565 A1 | 6/2002 | Barnea et al. | |
| 2002/0094533 A1 * | 7/2002 | Hess et al. | 435/6 |
| 2002/0103086 A1 | 8/2002 | Asrar et al. | 504/360 |
| 2002/0182258 A1 | 12/2002 | Lunsford et al. | |
| 2003/0022148 A1 | 1/2003 | Seki | |
| 2003/0031697 A1 * | 2/2003 | Chudzik et al. | 424/423 |
| 2003/0059468 A1 | 3/2003 | Mattern et al. | |
| 2003/0091971 A1 * | 5/2003 | Xia et al. | 435/2 |
| 2003/0119042 A1 | 6/2003 | Franco De Sarabia Rosado et al. | |
| 2003/0129755 A1 | 7/2003 | Sadler et al. | |

(56) References Cited

U.S. PATENT DOCUMENTS

| | | | |
|---|---|---|---|
| 2003/0138805 A1 | 7/2003 | Loffert et al. | |
| 2003/0157088 A1 | 8/2003 | Elliott et al. | |
| 2003/0162284 A1* | 8/2003 | Dordick et al. | 435/287.2 |
| 2003/0163608 A1 | 8/2003 | Tiwary et al. | 710/1 |
| 2003/0165482 A1* | 9/2003 | Rolland et al. | 424/93.21 |
| 2003/0175232 A1 | 9/2003 | Elliott et al. | |
| 2003/0199446 A1 | 10/2003 | Bunger et al. | |
| 2003/0215369 A1 | 11/2003 | Eggers et al. | 422/102 |
| 2004/0014068 A1 | 1/2004 | Burgoyne | |
| 2004/0101966 A1 | 5/2004 | Davis et al. | |
| 2004/0110267 A1 | 6/2004 | Sundar | |
| 2004/0121432 A1 | 6/2004 | Klein et al. | 435/69.1 |
| 2004/0142475 A1 | 7/2004 | Barman et al. | 435/459 |
| 2004/0208792 A1 | 10/2004 | Linton et al. | 422/99 |
| 2004/0228794 A1* | 11/2004 | Weller et al. | 424/1.11 |
| 2004/0241713 A1 | 12/2004 | Mirzabekov et al. | |
| 2005/0026181 A1 | 2/2005 | Davis et al. | |
| 2005/0053911 A1 | 3/2005 | Greener et al. | 435/2 |
| 2005/0086822 A1* | 4/2005 | Frisner et al. | 34/60 |
| 2005/0090009 A1 | 4/2005 | Cormier et al. | 435/459 |
| 2005/0112610 A1 | 5/2005 | Lee et al. | |
| 2005/0186254 A1 | 8/2005 | Roser et al. | |
| 2005/0196824 A1 | 9/2005 | Fiscer et al. | |
| 2005/0227269 A1 | 10/2005 | Lloyd, Jr. et al. | |
| 2005/0251501 A1 | 11/2005 | Phillips et al. | 707/2 |
| 2005/0276728 A1 | 12/2005 | Muller-Cohn et al. | |
| 2006/0014177 A1 | 1/2006 | Hogan et al. | |
| 2006/0099567 A1 | 5/2006 | Muller-Cohn et al. | |
| 2006/0127415 A1 | 6/2006 | Mayeresse | 424/234.1 |
| 2006/0147944 A1 | 7/2006 | Chomczynski et al. | |
| 2006/0177855 A1 | 8/2006 | Utermohlen et al. | |
| 2006/0193968 A1 | 8/2006 | Keogh et al. | |
| 2006/0198891 A1 | 9/2006 | Ravenelle et al. | |
| 2006/0293212 A1 | 12/2006 | Griese et al. | |
| 2007/0020289 A1 | 1/2007 | Mattern et al. | |
| 2007/0043216 A1 | 2/2007 | Bair, Jr. et al. | |
| 2007/0048726 A1 | 3/2007 | Baust et al. | |
| 2007/0073039 A1 | 3/2007 | Chisari | |
| 2007/0117173 A1 | 5/2007 | Levison et al. | |
| 2007/0135528 A1 | 6/2007 | Butler et al. | |
| 2008/0146790 A1 | 6/2008 | Grolz et al. | |
| 2008/0176209 A1 | 7/2008 | Muller et al. | 435/2 |
| 2008/0187924 A1 | 8/2008 | Korfhage et al. | |
| 2008/0268514 A1 | 10/2008 | Muller et al. | |
| 2008/0307117 A1 | 12/2008 | Muller-Cohn et al. | |
| 2009/0291427 A1 | 11/2009 | Muller-Cohn et al. | 435/2 |
| 2009/0298132 A1 | 12/2009 | Muller-Cohn et al. | 435/91.51 |
| 2009/0312285 A1 | 12/2009 | Fischer et al. | |
| 2011/0027862 A1 | 2/2011 | Bates et al. | |
| 2012/0052572 A1 | 3/2012 | Whitney et al. | |
| 2013/0209997 A1 | 8/2013 | Whitney et al. | |
| 2014/0065627 A1 | 3/2014 | Whitney et al. | |

FOREIGN PATENT DOCUMENTS

| | | |
|---|---|---|
| DE | 2424426 | 6/1973 |
| DE | 19834816 | 2/2000 |
| DE | 102008039734 | 3/2010 |
| EP | 0451924 | 10/1991 |
| EP | 0 448 146 B1 | 6/1994 |
| EP | 0 637 750 A2 | 2/1995 |
| EP | 0 706 825 A1 | 4/1996 |
| EP | 0774464 | 5/1997 |
| EP | 0 875 292 A1 | 11/1998 |
| EP | 0915167 | 5/1999 |
| EP | 0833611 B1 | 8/2001 |
| EP | 0 822 861 B1 | 11/2003 |
| EP | 1555033 A2 | 7/2005 |
| EP | 1082006 B1 | 2/2006 |
| EP | 1736542 | 12/2006 |
| EP | 1758932 | 3/2007 |
| EP | 1651712 B1 | 10/2007 |
| GB | 2 129 551 A | 5/1984 |
| JP | 62-502633 A | 10/1987 |
| JP | 08-211065 | 8/1996 |
| JP | 09-127106 A | 5/1997 |
| JP | 2001-50872 A | 2/2001 |
| WO | 86/07462 A1 | 12/1986 |
| WO | WO 87/00196 | 1/1987 |
| WO | WO 87/01206 | 2/1987 |
| WO | WO 89/00012 | 1/1989 |
| WO | WO 89/06542 | 7/1989 |
| WO | WO 90/05182 | 5/1990 |
| WO | WO 91/14773 | 10/1991 |
| WO | WO 92/00091 | 1/1992 |
| WO | WO 92/06188 | 4/1992 |
| WO | WO 92/06200 | 4/1992 |
| WO | WO 92/09300 | 6/1992 |
| WO | 9501559 A2 | 1/1995 |
| WO | WO95/02046 | 1/1995 |
| WO | 9510605 A1 | 4/1995 |
| WO | WO 95/16198 | 6/1995 |
| WO | WO 96/10640 | 4/1996 |
| WO | 9715394 A1 | 5/1997 |
| WO | 9815355 A2 | 4/1998 |
| WO | 9824543 A1 | 6/1998 |
| WO | 0014505 A1 | 3/2000 |
| WO | WO 00/20117 | 4/2000 |
| WO | WO 00/62023 | 10/2000 |
| WO | WO 00/76664 A1 | 12/2000 |
| WO | WO 01/94016 A1 | 12/2001 |
| WO | 03/020924 | 3/2003 |
| WO | 03/056293 | 7/2003 |
| WO | 2004112476 A1 | 12/2004 |
| WO | WO2005/059178 | 6/2005 |
| WO | WO2005/113147 | 12/2005 |
| WO | WO2005/116081 | 12/2005 |
| WO | 2006001499 A2 | 1/2006 |
| WO | 2007075253 A2 | 7/2007 |
| WO | 2007094581 A1 | 8/2007 |
| WO | WO2008/040126 | 4/2008 |
| WO | 2009002568 A2 | 12/2008 |
| WO | WO2009/009210 | 1/2009 |
| WO | WO 2009/038853 | 3/2009 |
| WO | WO2012/018639 | 2/2012 |

OTHER PUBLICATIONS

Carninci et al., "Thermostabilization and thermoactiviation of thermolabile enymes by trehalose and its application for the synthesis of full length cDNA," Proc. Natl. Acad. Sci. USA, 95:520-524, 1998.
Gombotz et al., "Biodegradable polymers for protein and peptide drug delivery," Bioconjugate Chem. 6(14):332-351, 1995.
Hoffman, "Hydrogels for biomedical applications," Adv. Drug Delivery Reviews 43(1):3-12, 2002.
Holland et al., "Biological sample collection and processing for molecular epidemiological studies," Mutation Research 543:217-234, 2003.
Holland et al., "Molecular epidemiology biomarkers—sample collection and processing considerations," Toxicol. and Appl. Pharm. 206(2):261-268, 2005.
Kaijalainen et al., "An alternative hot start technique for PCR in small volumes using beads of wax-embedded reaction components dried in trehalose," Nuc. Acid. Res. 21(12):2959-60, 1993.
Schyma, "Experiences with the polyvinyl alcohol method in forensic medicine practice," Arch Kriminol Jan.-Feb.;197 (1-2):41-6, 1996. (+English Abstract).
Schyma et al., "DNA-PCR Analysis of bloodstains sampled by polyvinyl-alcohol method," J. Forensic. Sci. 44(1):95-99, 1999.
Schyma et al., "The accelerated polyvinyl-alcohol method for GSR collection—PVAL 2.0," J. Forensic. Sci. 45 (6):1303-06, 2000.
Wang, "Instability, stabilization, and formulation of liquid protein pharmaceuticals," Int. J. Pharm. 185:129-88, 1999.
Wang, "Protein aggregation and its inhibition in biopharmaceutics," Int. J. Pharm, 289:1-30, 2005.
Whittlesey et al., "Delivery systems for small molecule drugs, proteins, and DNA: the neuroscience/biomaterial interface," Exp. Neurol. 190:1-16, 2004.
Anonymous, "Transmucosal Polymeric Molecular Delivery Systems," accessed Apr. 7, 2005, URL: http://www.antiagingresearch.com/hgh/transmucosal.php, 2 pages.

(56) References Cited

OTHER PUBLICATIONS

Bühler, B., et al., "Viral Evolution in Response to the Broad-based Retroviral Protease Inhibitor TL-3," *J Virol.*, 75(19):9502-8, Oct. 2001.

Dyke, C., et al., "Solvent-free Functionalization of Carbon Nanotubes," *J Am Chem Soc.*, 125(5):1156-7, Feb. 5, 2003.

Elzie, C., et al., "The N-terminus of Thrombospondin: The Domain Stands Apart," *Int J Biochem Cell Biol.*, 36(6):1090-101, Jun. 2004.

Garcia De Castro, A., et al., "Anhydrobiotic Engineering of Gram-negative Bacteria," *Appl Environ Microbiol.*, 66(9):4142-4, Sep. 2000.

Kirn-Safran, C., et al., "Heparan Sulfate Proteoglycans: Coordinators of Multiple Signaling Pathways During Chondrogenesis," *Birth Defects Res. (Part C)*, 72(1):69-88, Mar. 2004.

Langer, R., "New Methods of Drug Delivery," *Science*, 249(4976):1527-33, Sep. 28, 1990.

Langer, R., "Polymer-Controlled Drug Delivery Systems," *Accounts Chem. Res.* 26:537-542, 1993.

Lee, T., et al., "Analysis of the S3 and S3' Subsite Specificities of Feline Immunodeficiency Virus (FIV) Protease: Development of a Broad-based Protease Inhibitor Efficacious Against FIV, SIV, and HIV in Vitro and Ex Vivo," *Proc Natl Acad Sci USA.*, 95(3):939-44, Feb. 1998.

Lee, T., et al., "Development of a New Type of Protease Inhibitors, Efficacious Against FIV and HIV Variants," *J. Amer. Chem. Soc.*, 121:1145-1155, 1999.

Manzanera, M., et al., "Hydroxyectoine is Superior to Trehalose for Anhydrobiotic Engineering of *Pseudomonas putida* KT2440," *Appl Environ Microbiol.*, 68(9):4328-33, Sep. 2002.

Manzanera, M., et al., "Plastic Encapsulation of Stabilized *Escherichia coli* and *Pseudomonas putida*," *Appl Environ Microbiol.*, 70(5):3143-5, May 2004.

Mitchell, C., et al., "Dispersion of Functionalized Carbon Nanotubes in Polystyrene," *Macromolecules*, 35:8825-8830, 2002.

Ortega, N., et al., "New Functional Roles for Non-collagenous Domains of Basement Membrane Collagens," *J Cell Sci.*, 115(Pt 22):4201-14, Nov. 15, 2002.

Pavlov, I., et al., "The Role of ECM Molecules in Activity-dependent Synaptic Development and Plasticity," *Birth Defects Res. (Part C)*, 72(1):12-24, Mar. 2004.

Wierzbicka-Patynowski, I., et al., "The Ins and Outs of Fibronectin Matrix Assembly," *J Cell Sci.*, 116(Pt 16):3269-76, Aug. 15, 2003.

Yamamoto, Y., et al., "Molecular Design of Bioconjugated Cell Adhesion Peptide with a Water-soluble Polymeric Modifier for Enhancement of Antimetastatic Effect," *Curr Drug Targets*, 3(2):123-30, Apr. 2002.

Anchordoquy, Thomas J. and Marion C. Molina, "Preservation of DNA," Cell Preservation Technology, 5(4):180-188, Nov. 4, 2007.

Arakawa et al., "Small Molecule Pharmacological Chaperones: From Thermodynamic Stabilization to Pharmaceutical Drugs," Biochimica et Biophysica Acta, 1764:1677-1687, 2006.

Asano, Naoki, "Glycosidase Inhibitors: Update and Perspectives on Practical Use," Glycobiology, 13(10):93R-104R, 2003.

Cavalieri et al., "Chaperone-Like Activity of Nanoparticles of Hydrophobized Poly(vinyl alchohol)," Soft Matter, 3:718-724, 2007.

Dagani, Ron, "Stir, Heat—But No Need to Dissolve," Chemical & Engineering News, 81(5):5, Feb. 3, 2003.

Daugherty, Ann L. and Randall J. Mrsny, "Formulation and Delivery Issues for Monoclonal Antibody Therapeutics," Advanced Drug Delivery Reviews, 58:686-706, 2006.

Degim, I. Tuncer and Nevin Celebi, "Controlled Delivery of Peptides and Proteins," Current Pharmaceutical Design, 13:99-117, 2007.

Dong et al., "Biosynthesis of the Validamycins: Identification of Intermediates in the Biosynthesis of Validamycin a by *Streptomyces hygroscopicus* Var. Limoneus," Journal of the American Chemical Society, 123:2733-2742, Feb. 21, 2001.

Jones et al., "Long-Term Storage of DNA-Free RNA for Use in Vaccine Studies," BioTechniques, 43:675-681, Nov. 2007.

Kameda et al., "New Cyclitols, Degradation of Validamycin a by *Flavobacterium saccharophilum*," The Journal of Antibiotics, 33(12):1573-1574, Dec. 1980.

Knuesel et al., "Comparative Studies of Suidatrestin, a Specific Inhibitor of Trehalases," Comparative Biochemistry and Physiology Part B, 120:639-646, 1998.

Smith, Steve and Phillip A. Morin, "Optimal Storage Conditions for Highly Dilute DNA Samples: A Role for Trehalose as a Preserving Agent," Journal of Forensic Sciences, 50(5):1-8, Sep. 2005.

Wang et al., "Antibody Structure, Instability, and Formulation," Journal of Pharmaceutical Sciences, 96(1):1-26, Jan. 2007.

International Patent Application No. PCT/US2008/068628, filed Jun. 27, 2008, for "Integration of Sample Storage and Sample Management for Life Science".

U.S. Appl. No. 12/182,926, filed Jul. 30, 2008, Muller-Cohn et al.

Liao et al., "The effects of polyvinyl alcohol on the in vitro stability and delivery of spray-dried protein particles from surfactant-free HFA 134a-based pressurised metered dose inhalers," International Journal of Pharmaceutics 304:29-39, 2005.

Passot et al., "Physical characterisation of formulations for the development of two stable freeze-dried proteins during both dried and liquid storage," European Journal of Pharmaceutics and Biopharmaceutics 60:335-348, 2005.

Dankwardt et al., "Stabilization of enzyme immunoassays for atrazine," *Analytica Chimica Acta* 362:35-45, 1998.

El-Bashiti, "Trehalose Metabolism in Wheat and Identification of Trehalose Metabolizing Enzymes Under Abiotic Stress Conditions," Thesis, The Graduate School of Natural and Applied Sciences of the Middle East Technical University, Jul. 2003, 140 pages.

Komiyama et al., "Hydrolysis of DNA and RNA by lanthanide ions: mechanistic studies leading to new applications," *Chem. Commun.* 1443-1451, 1999.

Konishi et al., "Effects of Bay m 1099, an α-Glucosidase Inhibitor, on Starch Degradation in Germinating Mung Beans," *Biosci. Biotechnol. Biochem.* 62(1):142-144, 1998.

Allison et al., "Effects of Drying Methods and Additives on Structure and Function of Actin: Mechanisms of Dehydration-Induced Damage and Its Inhibition," Archives of Biochemistry and Biophysics 358(1):171-181, 1998.

Carpenter et al., "Stabilization of phosphofructokinase during air-drying with sugars and sugar/transition metal mixtures," Cryobiology 24(5):455-464, 1987 (Abstract only).

DePaz et al., "Effects of drying methods and additives on the structure, function, and storage stability of subtilisin: role of protein conformation and molecular mobility," Enzyme and Microbial Technology 31:765-774, 2002.

Prestrelski et al., "Dehydration-induced Conformational Transitions in Proteins and Their Inhibition by Stabilizers," Biophysical Journal 65:661-671, 1993.

Barnes, "The fidelity of Taq polymerase catalyzing PCR is improved by an N-terminal deletion," Gene 112:29-35 (1992).

Cheng et al., "Chip PCR. II. Investigation of different PCR amplification systems in microfabricated silicon-glass chips, " Nucleic Acids Res. 24:380-385 (1996).

Flaman et al., "A rapid PCR fidelity assay," Nucl. Acids Res., 22(15):3259-3260 (1994).

Godfrey, "Solvent selection via miscibility number," Chem. Technol. 2:359 (1972).

Kricka and Wilding, "Microchip PCR," Anal. Bioanal. Chem 377:820-825 (2003).

Lawyer et al., "High-level Expression, Purification, and Enzymatic Characterization of Full-length *Thermus aquaticus* DNA Polymerase and a Truncated Form Deficient in 5' to 3' Exonuclease Activity," PCR Meth. Appl. 2:275-287 (1993).

Lou et al., "Increased amplification efficiency of microchip-based PCR by dynamic surface passivation," Biotechniques, vol. 36, No. 2, pp. 248-252 (2004).

Luo et al., "Expression of a fusion protein of scFv-biotin mimetic peptide for immunoassay," J. Biotechnol. 65:225 (1998).

Mohr, "Reversible chemical reactions as the basis for optical sensors used to detect amines, alcohols and humidity," J. Mater. Chem., 9:2259-2264 (1999).

(56) References Cited

OTHER PUBLICATIONS

Muller-Cohn et al., "Integration of Sample Storage and Sample Management for Life Science," Amendment filed in U.S. Appl. No. 11/102,588, on Jan. 11, 2010, 21 pages.
Muller-Cohn et al., "Integration of Sample Storage and Sample Management for Life Science," Response filed in U.S. Appl. No. 11/102,588, on Aug. 18, 2009, 31 pages.
Muller-Cohn et al., "Integration of Sample Storage and Sample Management for Life Science," Response filed in U.S. Appl. No. 11/102,588, on Sep. 29, 2010, 28 pages.
Muller-Cohn et al., U.S. Appl. No. 11/102,588, Amendment filed on Apr. 1, 2011, 28 pages.
New England Biolabs 1993/1994.
PCT/US2005/012084 International Search Report dated Feb. 7, 2006.
Suslick et al., "Colorimetric sensor arrays for molecular recognition," Tetrahedron 60:11133-11138 (2004).
Ando et al., "PLGA Microspheres Containing Plasmid DNA: Preservation of Supercoiled DNA via Cryopreparation and Carbohydrate Stabilization," *Journal of Pharmaceutical Sciences* 88(1):126-130, 1999.
EP10775442.6 Extended European Search Report dated Jan. 21, 2014.
Goller et al, Protection of a model enzyme (lactate dehydrogenase) against heat, urea and freeze-thaw treatment by compatible solute additives, J. of Molecular Catalsys B: Enzymatic, 7(104):37-45 1999.
Iyer et al, Enzyme stability and stabilization-Aqueous and non-aqueous environment, Process Biochemistry, 43:1019-1032 (2008).
Baskakov et al., Forcing Thermodynamically Unfolded Proteins to Fold, The Journal of Biological Chemistry, 273(9):4831-4834, 1998.
Calbiochem® Inhibitor SourceBook™ 2004 (1st Ed.)), EMD Biosciences, La Jolla, CA.
Calbiochem® Inhibitor SourceBook™ 2007 (2nd Ed.), EMD Biosciences, La Jolla, CA.
Catalan et al., Progress towards a generalized solvent polarity scale: The solvatochromism of 2-(dimethylamino)-7-nitrofluorene and its homomorph 2-fluoro-7-nitrofluorene, Liebigs Ann. 1995(2):241-252 (1995).
Chen et al., Stabilization of Recombinant Human Keratinocyte Growth Factor by Osmolytes and Salts, Journal of Pharmaceutical Sciences, 85(4):419-426, 1996.
Cohen et al., Diffusion NMR Spectroscopy in Supramolecular and Combinatorial Chemistry: An Old Parameter—New Insights, Angew. Chem. Int. Ed., 44: 520-554 (2005).
De Sanctis et al., Influence of Glycerol on the Structure and Redox Properties of Horse Heart Cytochrome c. A Circular Dichroism and Electrochemical Study, Journal of Protein Chemistry, 15(7):599-606, 1996.
Di Tullio et al., Molecular recognition by mass spectrometry, J. Mass Spectrom, 40(7):845-865 (2005).
Dowell et al. Otitis media—principles of judicious use of antimicrobial agents. Pediatrics. 1998; 101 Suppl. 1: 165-171.
Dowell et al. Principles of judicious use of antimicrobial agents for pediatric upper respiratory tract infections. Pediatrics. 1998; 101 Suppl. 1: 163-165.
EP08826300.9 Supplementary Search Report dated Oct. 26, 2010.
EP11815081.2 Extended European Search Report dated Nov. 5, 2013.
EP11815082.0 Extended European Search Report dated Nov. 5, 2013.
Frye et al., The kinetic basis for the stabilization of staphylococcal nuclease by xylose, Protein Science, 6:789-793, 1997.
Galinski et al., 1,4,5,6-Tetrahydro-2-methyl-4-pyrimidinecarboxylic acid. A novel cyclic amino acid from halophilic phototrophic bacteria of the genus *Ectothiorhodospira*, Eur. J. Biochem., 149:135-139, 1985.
Green DR, Apoptosis. Death deceiver, Nature, 396(6712):629-30 (1998).
Green DR, Apoptotic pathways: the roads to ruin, Cell, 94(6):695-69 (1998).
Green et al., Mitochondria and apoptosis, Science, 281(5381):1309-12 (1998).
Knapp et al., Extrinsic protein stabilization by the naturally occurring osmolytes β-hydroxyectoine and betaine, Extremophiles, 3:191-198, 1999.
Kumar et al., The role of proline in the prevention of aggregation during protein folding in vitro, Biochemistry and Molecular Biology International, 46(3):509-517, 1998.
Li et al., Effect of Mobile Phase Additives on the Resolution of Four Bioactive Compounds by RP-HPLC, Int'l Journal of Molecular Sciences, 11(5):2229-2240 (Jan. 2010).
Loo et al., Peptide and Protein Analysis by Electrospray Ionization—MassSpectrometry and Capillary Electrophoresis-Mass Spectrometry, Anal. Biochem., 179(2):404-412 (1989).
Lozano et al., Stabilization of a-Chymotrypsin by Ionic Liquids in Transesteri cation Reactions, Biotechnology and Bioengineering, 75(5):563-569 (Dec. 2001).
Malin et al., Effect of Tetrahydropyrimidine Derivatives on Protein-Nucleic Acids Interaction, The Journal of Biological Chemistry, 274(11):6920-6929, 1999.
Marshall et al., NXY-059, a Free Radical—Trapping Agent, Substantially Lessens the Functional Disability Resulting From Cerebral Ischemia in a Primate Species, Stroke, 32:190-198 (2001).
Mascellani et al., Compatible solutes from hyperthermophiles improve the quality of DNA microarrays, BMC Biotechnology, 7(82):1-6, 2007.
O'Brien et al. Acute sinusitis—principles of judicious use of antimicrobial agents. Pedatrics. 1998; 101 Suppl. 1: 174-177.
O'Brien et al. Cough illness/bronchitis—principles of judicious use of antimicrobial agents. Pediatrics. 1998; 101 Suppl. 1: 178-181.
Parsegian et al., Macromolecules and Water: Probing with Osmotic Stress, Methods in Enzymology, 259:43-94, 1995.
PCT/US2005/012084 International Preliminary Report on Patentability dated Oct. 11, 2006.
PCT/US2006/45661 International Preliminary Report on Patentability dated Jun. 30, 2008.
PCT/US2006/45661 International Search Report and Written Opinion dated Nov. 13, 2007.
PCT/US2008/061332 International Preliminary Report on Patentability dated Oct. 27, 2009.
PCT/US2008/061332 International Search Report and Written Opinion dated Jul. 29, 2009.
PCT/US2008/068628 International Preliminary Report on Patentability dated Jan. 5, 2010.
PCT/US2008/068628 International Search Report and Written Opinion dated Aug. 27, 2009.
PCT/US2010/34454 International Preliminary Report on Patentability dated Nov. 15, 2011.
PCT/US2010/34454 International Search Report and Written Opinion dated Jan. 20, 2011.
PCT/US2011/045404 International Preliminary Report on Patentability dated Jan. 29, 2013.
PCT/US2011/045404 International Search Report and Written Opinion dated Mar. 27, 2012.
PCT/US2011/045405 International Preliminary Report on Patentability dated Jan. 29, 2013.
PCT/US2011/045405 International Search Report and Written Opinion dated Mar. 26, 2012.
Roberts, Organic compatible solutes of halotolerant and halophilic microorganisms, Saline Systems, 1(5):1-30, 2005.
Rosenstein et al. The common cold—principles of judicious use of antimicrobial agents. Pediatrics. 1998; 101 Suppl. 1: 181-184.
Russell et al., Principles and Practice of Disinfection, Preservation and Sterilization, (Eds.), 1999, Blackwell Science, Malden, MA.
Sauer et al., Bacterial Milking: A Novel Bioprocess for Production of Compatible Solutes,Biotechnology and Bioengineering, 57(3):306-313, 1998.
Schwartz et al. Pharyngitis—principles of judicious use of antimicrobial agents. Pediatrics. 1998; 101 Suppl. 1: 171-174.
Scouten, A survey of enzyme coupling techniques, Methods in Enzymology, 135:30-65 (1987).
Sirieix-Plenet et al., Behaviour of a binary solvent mixture constituted by an amphiphilic ionic liquid, 1-decyl-3-methylimidazolium

(56) References Cited

OTHER PUBLICATIONS bromide and water Potentiometric and conductimetric studies, Talanta 63(4):979-986, Jul. 8, 2004.

Slita et al., DNA-polycation complexes Effect of polycation structure on physico-chemical and biological properties, Journal of Biotechnology, 127:679-693, 2007.

Sola-Penna et al., Carbohydrate protection of enzyme structure and function against guanidinium chloride treatment depends on the nature of carbohydrate and enzyme, Eur. J. Biochem., 248:24-29, 1997.

Timasheff, Water as Ligand: Preferential Binding and Exclusion of Denaturants in Protein Unfolding, Biochemistry, 3/(40:9857-9864, 1992.

Vanin, Iron diethyldithiocarbamate as spin trap for nitric oxide detection, Meth. Enzymol., 301:269-79 (1999).

Voziyan et al., Chaperonin-assisted folding of glutamine synthetase under nonpermissive conditions: Off-pathway aggregation propensity does not determine the co-chaperonin requirement, Protein Science, 9:2405-2412, 2000.

Wang et al., A Naturally Occurring Protective System in Urea-Rich Cells: Mechanism of Osmolyte Protection of Proteins against Urea Denaturation, Biochemistry, 36:9101-9108, 1997.

Whitman et al., Prokaryotes: the unseen majority, Proc. Natl. Acad. Sci. USA, 95:6578-83 (1998).

Yancey et al., Living with Water Stress: Evolution of Osmolyte Systems, Science, 217:1214-1222, 1982.

Yang et al., Neuroprotection by 2-h postischemia administration of two free radical scavengers, alpha-phenyl-n-tert-butyl-nitrone (PBN) and N-tert-butyl-(2-sulfophenyl)-nitrone (S-PBN), in rats subjected to focal embolic cerebral ischemia., Exp. Neurol., 163(1):39-45 (2000).

Zhao et al., NXY-059, a novel free radical trapping compound, reduces cortical infarction after permanent focal cerebral ischemia in the rat, Brain Res., 909(1-2):46-50 (2001).

Zhi et al., Renaturation of citrate synthase: Influence of denaturant and folding assistants, Protein Science, 1:522-529, 1992.

U.S. Appl. No. 12/509,303 Final Office action dated Jun. 9, 2014.

U.S. Appl. No. 11/291,267 Office action dated Jun. 13, 2014.

U.S. Appl. No. 12/182,926 Office action dated Apr. 30, 2014.

\* cited by examiner

INTEGRATION OF SAMPLE STORAGE AND SAMPLE MANAGEMENT FOR LIFE SCIENCE

CROSS-REFERENCE TO RELATED APPLICATION

This application claims the benefit of U.S. Provisional Patent Application No. 60/560,829, filed Apr. 8, 2004, which is incorporated herein by reference in its entirety.

TECHNICAL FIELD

The present invention relates generally to processes by which biological materials and samples are received and placed into inventory systems. The invention also relates to the use, organization, storage, tracking, retrieval and analysis of such biological materials and samples and to the automation of these processes.

BACKGROUND OF THE INVENTION

Research in the life sciences field is based upon the analysis of biological materials and samples, such as DNA, RNA, blood, urine, buccal swabs, bacteria, viruses, PCR products, cloned DNA, proteins, cells and tissues, and of minerals or chemicals. Such samples are typically collected or obtained from appropriate sources and placed into storage and inventory for further processing and analysis.

Storage containers for such samples include bottles, tubes, vials, bags, boxes, racks, multi-well dishes and multi-well plates which are typically sealed by individual screw caps or snap caps, snap or seal closures, lids, adhesive strips or tape, or multi-cap strips. The standard container format for medium to high throughput of sample storage, processing and automation of biological processes is a 96-, 384-, or 1536-well plate or array. The containers and the samples contained therein are stored at various temperatures, for example at ambient temperature or at 4° C. or at temperatures below 0° C., typically at about −20° C. or at −70° C. to −80° C. The samples that are placed and stored in the devices are most frequently contained in liquid medium or a buffer solution, and they require storage at such subzero temperatures (e.g., −20° C. or −70 to −80° C.). In some cases, samples are first dried and then stored at ambient temperature, or at 4° C., at −20° C. or at −70 to −80° C.

For example, presently, nucleic acids are stored in liquid form at low temperatures. For short term storage, nucleic acids can be stored at 4° C. For longterm storage the temperature is generally lowered to −20° C. to −70° C. to prevent degradation of the genetic material, particularly in the case of genomic DNA and RNA. Nucleic acids are also stored at room temperature on solid matrices such as cellulose membranes. Both storage systems are associated with disadvantages. Storage under low temperature requires costly equipment such as cold rooms, freezers, electric generator back-up systems; such equipment can be unreliable in cases of unexpected power outage or may be difficult to use in areas without a ready source of electricity or having unreliable electric systems. The storage of nucleic acids on cellulose fibers also results in a substantial loss of material during the rehydration process, since the nucleic acid stays trapped by, and hence associated with, the cellulose fibers instead of being quantitatively recoverable. Nucleic acid dry storage on cellulose also requires the separation of the cellulose from the biological material, since the cellulose fibers otherwise contaminate the biological samples. The separation of the nucleic acids from cellulose filters requires additional handling, including steps of pipetting, transferring of the samples into new tubes or containers, and centrifugation, all of which can result in reduced recovery yields and increased opportunity for the introduction of unwanted contaminants or exposure to conditions that promote sample degradation, and which are also cost- and labor-intensive.

Proteins are presently handled primarily in liquid stages, in cooled or frozen environments typically ranging from −20° C. to storage in liquid nitrogen. In some exceptions proteins may be freeze-dried, or dried at room temperature in the presence of trehalose and applied directly to an untreated surface. (Garcia de Castro et al., 2000 *Appl. Environ. Microbiol.* 66:4142; Manzanera et al., 2002 *Appl. Environ. Microbiol.* 68:4328) Proteins often degrade and/or lose activity even when stored cooled (4° C.), frozen (−20° C. or −80° C.). The freeze-thaw stress on proteins reduces bioactivity (e.g., enzymatic activity, specific binding to a cognate ligand, etc.) especially if repeated freeze-thawing of aliquots of a protein sample is required. The consequent loss of protein activity that may be needed for biological assays typically requires the readjustment of the protein concentration in order to obtain comparable assay results, or costly rejection of compromised protein reagents in favor of procuring new lots. The common practice of having multiple uses of enzyme reagents stored in a laboratory, especially by different users at different times and employing non-standardized handling procedures, further reduces the reliability of experimental data generated with such reagents. As a result, the half-life of proteins is reduced and expensive reagents have to be replaced frequently, amounting to enormous financial costs to the user. For the supplier of the proteins high costs are required to maintain an undisrupted frozen supply chain starting with initial cold room work-ups, for shipment, frozen storage of the sample, and frozen transport of the protein from production to the site of use. For example, delays during shipment can result in inactivation of proteins, which then have to be replaced at great cost to the supplier; receipt of inactive product can also result in dissatisfied customers.

Drying of proteins, and nucleic acids has yet to be universally adopted by the research scientific, biomedical, biotechnology and other industrial business communities because of the lack of standard established and reliable processes, difficulties with recoveries of quantitative and functional properties, variable buffer and solvent compatibilities and tolerances, and other difficulties arising from the demands of handling nucleic acids and proteins. The same problems apply to the handling, storage, and use of other biological materials, such as viruses, phage, bacteria, cells and multicellular organisms.

Present sample storage containers represent a multitude of platforms with no unified approach to sample preparation, sample storage, sample inventory, sample tracking, sample retrieval and sample analysis. It is clear that none of the current sample processing and storage formats solve problems that arise from individual storage containers, inadequate closure and containment aids, sample contamination, inadequate organization, diverse labeling systems, large space and storage requirements and temperature constraints.

The genomic age and the recent deciphering of the human and many other genomes, proteomes, transcriptomes, etc. have led to the industrialization of life sciences research. Millions of biological samples including genes and/or gene products from a multitude of organisms are being analyzed in order to advance scientific knowledge and develop commercial products. The development of high throughput technologies has resulted in a vast pool of information and samples, such that there is a need to integrate sample storage, data organization and data analysis. The generation of myriad biological samples and data consequently poses a significant organizational challenge to small and large laboratories. Previously available data management options for life sciences samples, such as LIMS (Laboratory Information Management Systems), are incapable of integrating information pertaining to a particular sample or samples with a sample storage device, and typically store sample data on a central server that is neither physically nor electronically connected to the sample storage device. Moreover, such previously available systems require inconvenient storage rack configurations, typically involving cumbersome cold storage and/or costly, complex software that requires a dedicated full-time Information Technologies support professional regardless of whether a large-scale enterprise software system is to be purchased and configured to a particular user's needs, or if instead a customized program is to be independently developed.

Clearly there is a need in the industry for universal life sciences sample storage, retrieval, analysis and information-matching devices and systems. The present disclosure addresses such needs by providing a plurality of life sciences sample storage and data applications, and offers other related advantages.

SUMMARY OF THE INVENTION

It is an aspect of the present invention to provide a system for processing data regarding the storage, organization, tracking, retrieval, and analysis of biological samples, the system including a biological sample device; a computer-implemented system for receiving, storing, processing, and communicating data regarding the sample device; and a radio frequency interface between the sample device and the computer-implemented system for providing a communication link between the computer-implemented system and the sample device.

According to the several embodiments of the invention, there are provided the following: A biological sample storage device for one or a plurality of biological samples, comprising: (a) a lid; (b) a sample plate comprising one or a plurality of sample wells that are capable of containing a biological sample, wherein one or more of said wells comprises a matrix material; and (c) at least one radio frequency transponder device. A related biological sample storage device wherein the matrix material dissolves or dissociates in a solvent or which comprises a closure means for closing the lid onto the sample plate, optionally wherein further the closure means comprises a magnetic closure. A related biological sample storage device which comprises an airtight closure joint, or comprising an airtight closure joint around each well, or comprising a magnetic closure and an airtight closure joint around each well. In certain embodiments there is provided a related biological sample storage device wherein the matrix material is capable of dry storage of the sample without refrigeration.

In other embodiments the invention provides a biological sample storage device for one or a plurality of biological samples, comprising (a) a lid; (b) a sample plate comprising one or a plurality of sample wells that are capable of containing a biological sample, wherein one or more of said wells comprises a matrix material that dissolves or dissociates in a solvent; and (c) at least one radio frequency transponder device. In certain further embodiments of the above described biological sample storage device, at least one well comprises at least one detectable indicator, which in certain further embodiments comprises a calorimetric indicator, and which in certain other embodiments is a fluorescent indicator, a luminescent indicator, a phosphorescent indicator, a radiometric indicator, a dye, an enzyme, a substrate of an enzyme, an energy transfer molecule, or an affinity label. In certain other further embodiments the detectable indicator is capable of detectably indicating presence of at least one of an amine, an alcohol, an aldehyde, water, a thiol, a sulfide, a nitrite, avidin, biotin, an immunoglobulin, an oligosaccharide, a nucleic acid, a polypeptide, an enzyme, a cytoskeletal protein, a reactive oxygen species, a metal ion, pH, $Na^+$, $K^+$, $Cl^-$, a cyanide, a phosphate and selenium. In certain other further embodiments the detectable indicator is selected from the group consisting of phenol red, ethidium bromide, a DNA polymerase, a restriction endonuclease, cobalt chloride, Reichardt's dye and a fluorogenic protease substrate.

According to certain other related embodiments the biological sample storage device comprises at least one well that comprises at least one inhibitor that is a biological inhibitor or a biochemical inhibitor, which may be validamycin A, TL-3, sodium orthovanadate, sodium fluoride, N-α-tosyl-Phe-chloromethylketone, N-α-tosyl-Lys-chloromethylketone, aprotinin, phenylmethylsulfonyl fluoride, diisopropylfluoro-phosphate, a kinase inhibitor, a phosphatase inhibitor, a caspase inhibitor, a granzyme inhibitor, a cell adhesion inhibitor, a cell division inhibitor, a cell cycle inhibitor, a lipid signaling inhibitor and a protease inhibitor, a reducing agent, an alkylating agent, or an antimicrobial agent. In certain embodiments the matrix material is capable of dry storage of the sample without refrigeration, in certain embodiments the matrix material comprises polyvinyl alcohol, and in certain other embodiments the matrix material comprises at least one material selected from polyethylene glycol, agarose, poly-N-vinylacetamide, polyvinylpyrrolidone, poly(4-vinylpyridine), polyphenylene oxide, crosslinked acrylamide, polymethacrylate, carbon nanotube, polylactide, lactide/glycolide copolymer, hydroxymethacrylate copolymer, calcium pectinate, hydroxypropyl methylcellulose acetate succinate, heparin sulfate proteoglycan, hyaluronic acid, glucuronic acid, thrombospondin-1 N-terminal heparin-binding domain, fibronectin, a peptide/water-soluble polymeric modifier conjugate, collagen, hydroxyectoine, polystyrene or trehalose. In another embodiment the invention provides a kit, comprising (I) a biological sample storage device for one or a plurality of biological samples, comprising (a) a lid; (b) a sample plate comprising one or a plurality of sample wells that are capable of containing a biological sample, wherein one or more of said wells comprises a matrix material; and (c) at least one radio frequency transponder device; and (II) one or more ancillary reagents. In certain further embodiments the matrix material dissolves or dissociates in a solvent Turning to another embodiment of the invention, there is provided a method of storing one or a plurality of biological samples, comprising contacting one or a plurality of biological samples with a biological sample storage device, said biological sample storage device comprising (i) a lid, (ii) a sample plate comprising one or a plurality of sample wells that are capable of containing a biological sample, wherein one or more of said wells comprises a matrix material, and (iii) at least one radio frequency transponder device, and thereby storing said biological samples, the method in certain further embodiments comprising maintaining the biological sample storage device without refrigeration subsequent to the step of contacting. Another invention embodiment provides a method of storing one or a plurality of biological samples, comprising (a) contacting one or a plurality of biological samples with a biological sample storage device, said biological sample storage device comprising (i) a lid, (ii) a sample plate comprising one or a plurality of sample wells that are capable of containing a biological sample, wherein one or more of said wells comprises a matrix material that dissolves or dissociates in a solvent, and (iii) at least one radio frequency transponder device; and (b) drying one or more of the sample wells, and thereby storing said biological samples, the method in certain further embodiments comprising maintaining the biological sample storage device without refrigeration subsequent to the steps of contacting and drying, wherein in certain still further embodiments biological activity of the sample subsequent to the step of maintaining is substantially the same as biological activity of the sample prior to the step of contacting, and wherein in certain other still further embodiments degradation of the biological sample is decreased relative to degradation of a control biological sample maintained without refrigeration in the absence of the matrix material. In certain related embodiments the step of contacting comprises simultaneously dissolving or dissociating the matrix material in a solvent, while in certain other related embodiments the step of contacting is preceded by dissolving or dissociating the matrix material in a solvent, while in certain other related embodiments the step of contacting is followed by dissolving or dissociating the matrix material in a solvent.

In another embodiment the invention provides a method of preparing a biological sample storage device for one or a plurality of biological samples, comprising (a) administering a matrix material that dissolves or dissociates in a solvent to one or a plurality of sample wells of a biological sample storage device, wherein said biological sample storage device comprises (i) a lid, (ii) a sample plate comprising one or a plurality of sample wells that are capable of containing a biological sample, and (iii) at least one radio frequency transponder device; and (b) drying one or more of the sample wells, and thereby preparing the biological sample storage device. In certain further embodiments the step of administering comprises administering a liquid solution or a liquid suspension that contains the matrix material and the solvent, while in certain other further embodiments at least one well comprises at least one detectable indicator, while in certain other further embodiments at least one well comprises at least one inhibitor that is a biological inhibitor or a biochemical inhibitor.

In another embodiment there is provided a method of recovering a stored biological sample, comprising (a) contacting, simultaneously or sequentially and in either order in a biological sample storage device, one or a plurality of biological samples with a matrix material, said biological sample storage device comprising (i) a lid, (ii) a sample plate comprising one or a plurality of sample wells that are capable of containing the biological sample, wherein one or more of said wells comprises the matrix material and wherein the matrix material dissolves or dissociates in a first solvent, and (iii) at least one radio frequency transponder device; (b) drying one or more of the sample wells; (c) maintaining the biological sample storage device without refrigeration subsequent to the steps of contacting and drying; and (d) resuspending or redissolving the biological sample in a second solvent, and therefrom recovering the stored biological sample, wherein in a certain further embodiment biological activity of the sample subsequent to the step of maintaining is substantially the same as biological activity of the sample prior to the step of contacting, while in a different further embodiment the second solvent is selected from (i) a solvent that is the same as the first solvent and (ii) a solvent that is different from the first solvent. In a certain related embodiment, at least one of the first solvent and the second solvent is an activity buffer.

In another embodiment the present invention provides a system for processing data regarding the storage, organization, tracking, retrieval, and analysis of biological samples, the system comprising: a biological sample device; a computer-implemented system for receiving and transmitting data regarding the sample device; and a radio frequency interface between the sample device and the computer-implemented system for providing a communication link between the computer-implemented system and the sample device. In a further embodiment the computer-implemented system comprises a data structure for maintaining data regarding the storage, organization, tracking, retrieval, and analysis of biological samples associated with the sample device. In a related embodiment the radio frequency interface comprises a radio frequency interrogator coupled to the computer-implemented system and at least one transponder device associated with the sample device for radio frequency communication with the interrogator.

In another embodiment there is provided a method for processing data regarding the storage, organization, tracking, retrieval, and analysis of biological samples, the method comprising: providing a sample device for storing one or more biological samples; providing a computer-implemented system for receiving, storing, and transmitting data regarding the sample device or the biological sample or both; providing a radio frequency communication interface between the sample device and the computer-implemented system. In a further embodiment the method comprises generating control signals from the computer-implemented system to cause the radio frequency interface to retrieve data from the sample device, and in a distinct further embodiment the method comprises generating control signals by the computer-implemented system to transmit data to the sample device via the radio frequency interface.

According to another embodiment, the invention provides a system for processing data regarding the storage, organization, tracking, retrieval, and analysis of biological samples, the system comprising a biological sample storage device, said sample storage device comprising a lid; a sample plate comprising one or a plurality of sample wells that are capable of containing a biological sample; and at least one radio frequency transponder device; a computer-implemented system for receiving and transmitting data regarding the sample storage device; and a radio frequency interface between the sample device and the computer-implemented system for providing a communication link between the computer-implemented system and the sample device. In certain further embodiments the computer-implemented system comprises a 3-tier architecture having a web browser, a web server program, and a database server, and a client-side application that controls operation of the radio frequency interface, and in certain still further embodiments the system comprises a USB interface between the web browser and an RFID reader. In another related embodiment the computer-implemented system comprises a 2-tier architecture having an Excel macro program on a client side and a database server. In another related embodiment the computer-implemented system comprises a 2-tier architecture having a stand-alone client application and a database server in communication with the client application. In certain further embodiments the client application is a compiled application.

In another embodiment, the present invention provides a biological sample storage device for one or a plurality of biological samples, comprising (a) a lid (b) a sample plate comprising one or a plurality of sample wells that are capable of containing a biological sample; and (c) at least one radio frequency transponder device. In a further embodiment the biological sample storage device comprises a closure means for closing the lid onto the sample plate, and in certain further embodiments the closure means comprises a magnetic closure. In another embodiment the biological sample storage device which comprises an airtight closure joint, and in another embodiment the storage device comprises an airtight closure joint around each well. In another embodiment the biological sample storage device comprises a magnetic closure and an airtight closure joint around each well.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
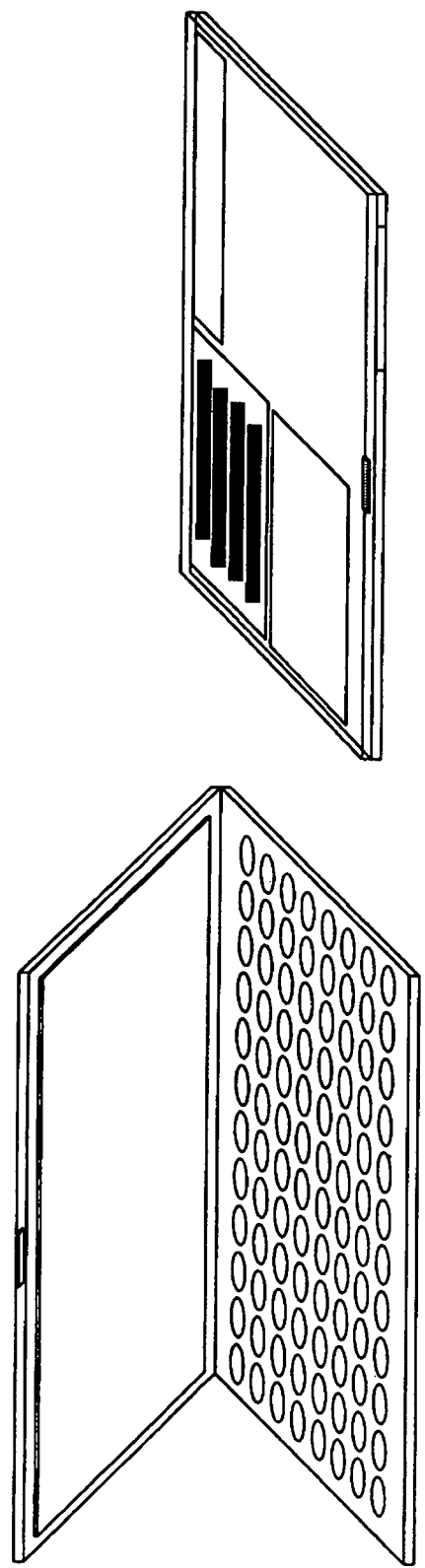
FIG. 1 is a schematic diagram of a sample plate for dry storage of biological materials.
Figure 2:
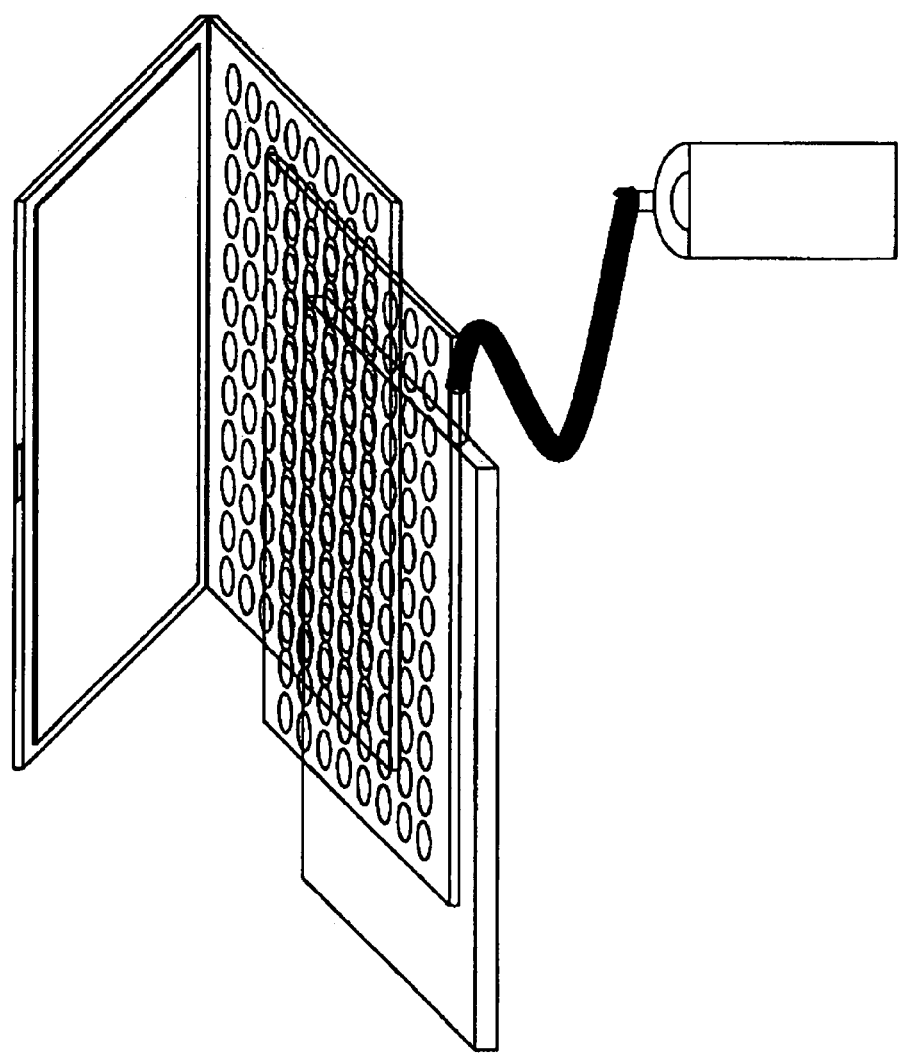
FIG. 2 is a schematic diagram of the air pressure unit and its interlocking modules.
Figure 3:
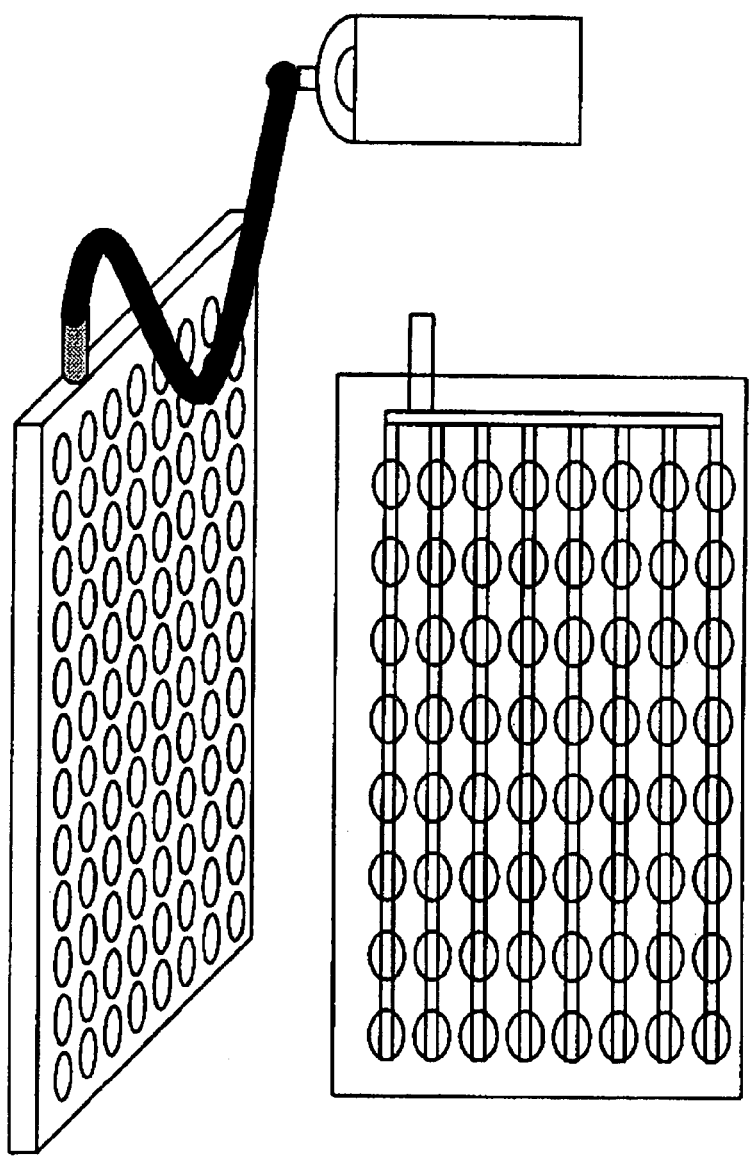
FIG. 3 is a schematic diagram of the air pressure unit's air channels.
Figure 4:
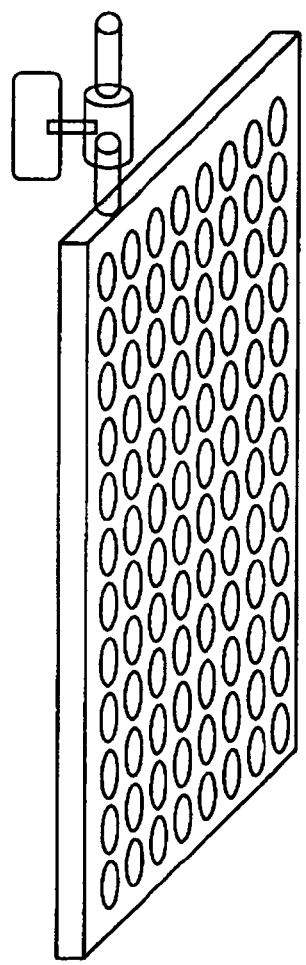
FIG. 4 is a schematic diagram of the air pressure unit and its regulation air valve.
Figure 4:
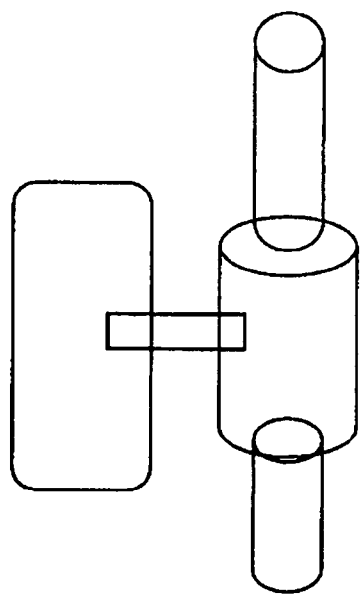
Figure 5:
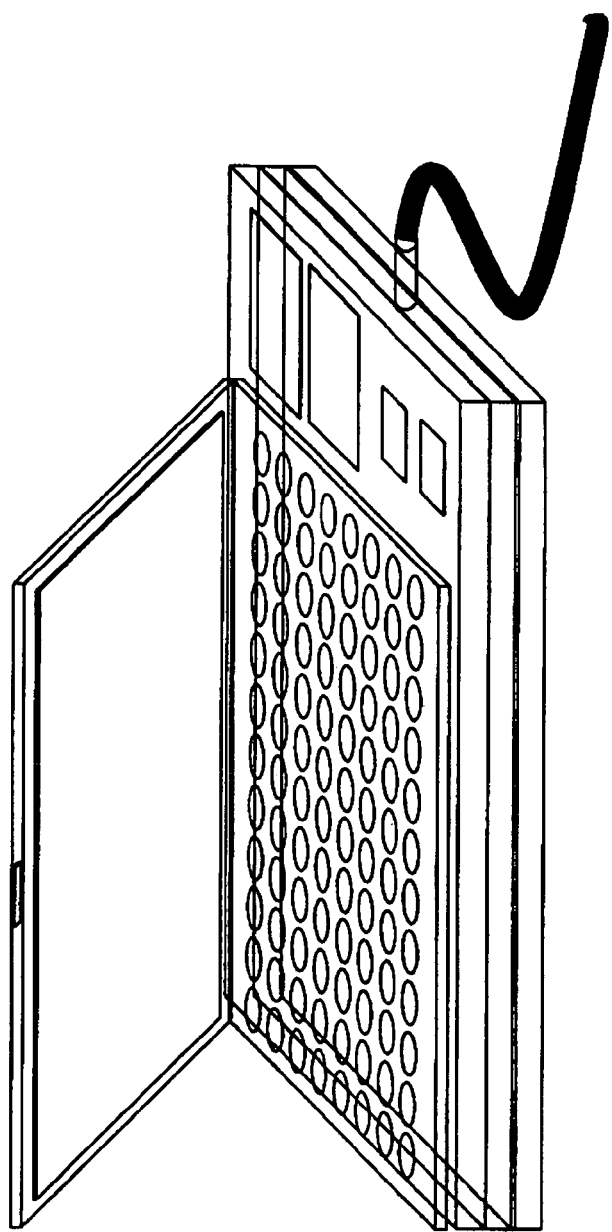
FIG. 5 is a schematic diagram of a portable PCR device to provide reagents for a sample plate.
Figure 6:
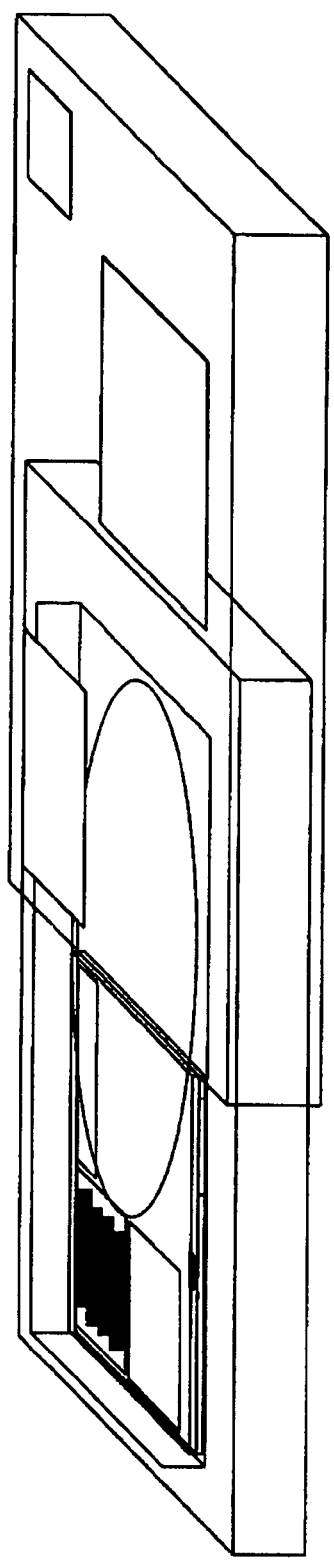
FIG. 6 is a schematic diagram of the shipping sleeve.
Figure 7:
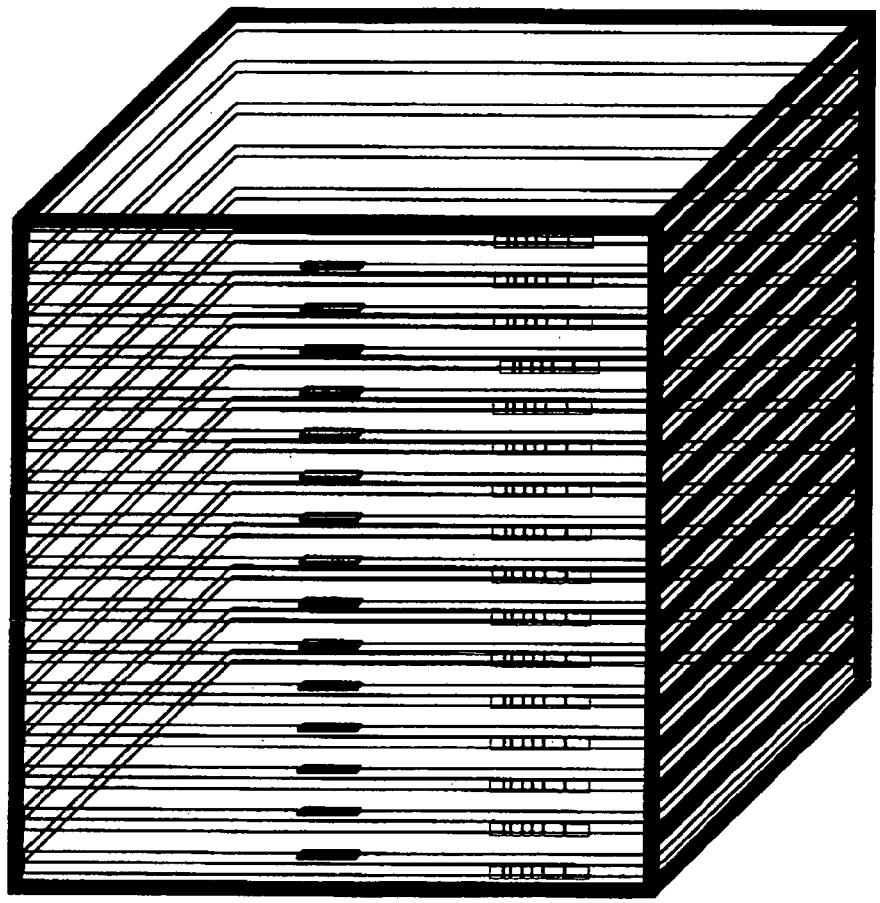
FIG. 7 is a schematic diagram of the stacking rack.
Figure 8:
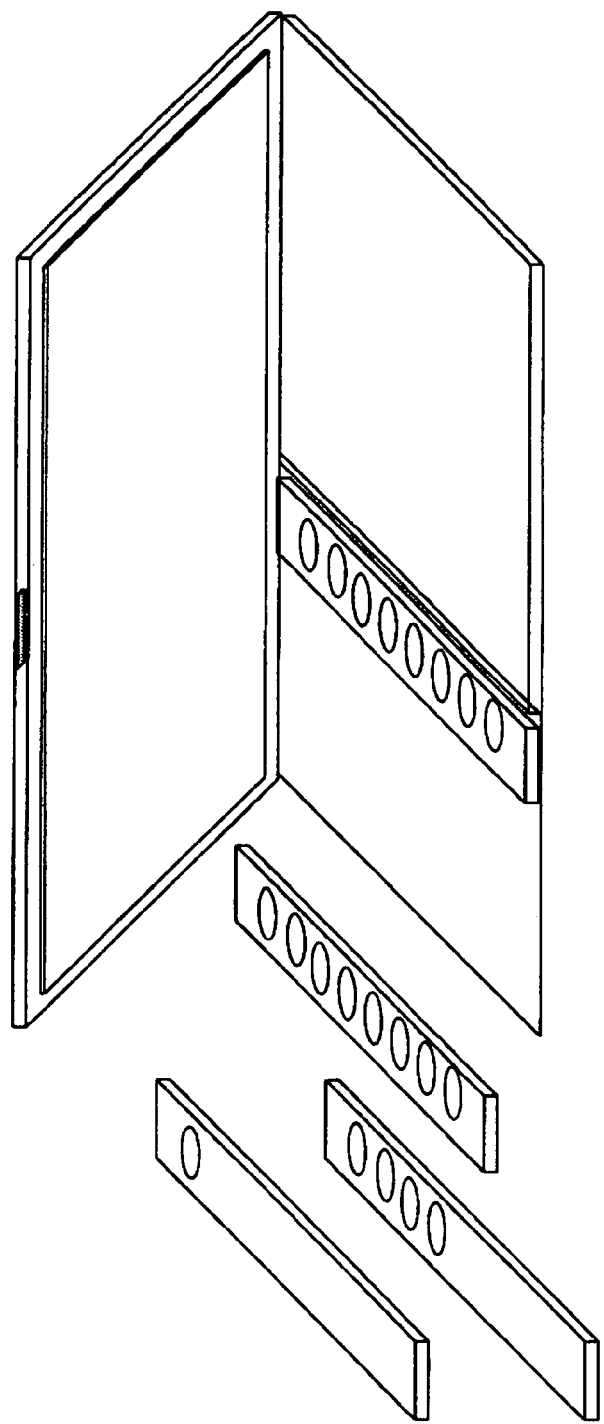
FIG. 8 is a schematic diagram of the sample storage strip well plate.

The present invention relates to a multi-component system and method for the isolation, purification, preservation, storage, tracking, retrieval, data matching, monitoring and/or analysis of biological samples and biological materials, minerals and chemicals as described herein. The invention may be used for storage of dry samples and for storage at ambient temperature, and also may have use for the storage of diverse biological materials and samples, such as but not limited to DNA, RNA, blood, urine, other biological fluids (e.g., serum, serosal fluids, plasma, lymph, cerebrospinal fluid, saliva, mucosal secretions of the secretory tissues and organs, vaginal secretions, ascites fluids, fluids of the pleural, pericardial, peritoneal, abdominal and other body cavities, cell and organ culture medium including cell or organ conditioned medium, lavage fluids and the like, etc.) buccal swabs, bacteria, viruses, PCR products, cloned DNA, proteins, cells and tissues, or other biological samples. Biological samples may therefore include a blood sample, biopsy specimen, tissue explant, organ culture, biological fluid or any other tissue or cell preparation, or fraction or derivative thereof or isolated therefrom, from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like.

In certain embodiments, the invention thus relates to the longterm storage of biological, chemical and biochemical material under dry conditions, and in a manner ready for immediate use after hydration (e.g., upon rehydration). As described herein, there are provided embodiments which include a) the specific dissolvable (or dissociatable) storage matrix, b) preparation and optimization of the storage matrix with chemicals that increase the durability of the longterm storage conditions, c) preparation of different biological materials prior to the drying process that allow immediate, activity and usability of the materials after hydration, and d) the process of simplifying complex biochemical processes through the use of dry stored biologically active materials. These and related embodiments thus provide surprising advantages associated with unrefrigerated dry storage of biologicals, including improved stabilization and preservation of biological activity in biological samples, reduced degradation of biological samples during storage at room temperature in dried form (and in particular through the use of a protective matrix), and simplification of the processes for preparing biological samples for further use by reducing or eliminating the need for time-consuming re-calibration and aliquoting of such samples.

The invention allows for purification and size fractionation of DNA, RNA, cells, cellular components and other biological materials, minerals, chemicals, or compositions derived from a biological sample or other life sciences related sample. The invention thus readily permits, for example, the use of one or a plurality of biological materials and/or biological samples in the performance of molecular biology procedures, including but not limited to PCR, biopolymer (e.g., polynucleotide, polypeptide, or other biopolymer) sequencing, oligonucleotide primer extension, haplotyping (e.g., DNA haplotyping) and restriction mapping in one unified, integrated and easy-to-use platform. The invention also readily permits, for example and in certain embodiments, the use of one or a plurality of biological samples and/or biological materials for the performance of protein crystallography. In other embodiments there is provided a platform for use, testing or detection (including diagnostic applications) of an antibody or small molecule (whether naturally occurring or artificial) or other biological molecule, for example, a protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or another biological molecule that is a constituent of a biological sample.

The Biological Sample Storage Device

The biological sample storage device ("storage device") of the present invention is comprised of a sample plate and a lid. The dimensions of the storage device may be from about 2 mm to about 25 mm in height, about 80 mm to about 200 mm in length, and about 60 mm to about 150 mm in width. Preferably, the storage device has a height of about 3 mm to about 15 mm, a length of about 100 mm to about 140 mm, and a width of about 60 mm to about 100 mm. The storage device may be made out of colorful polypropylene and may hold as many as 96, 384, 1536 or more sample deposit wells. Each storage device has its own tight sealing lid. The storage device may be manufactured by injection molding and can be made in one piece or in multiple pieces.

In preferred embodiments and as described herein, the biological sample storage device is configured for use in a system for processing sample data that comprises a radio frequency interface between the storage device and a computer-implemented system for receiving, storing and/or transmitting data. The data may pertain to the storage device and/or to the one or more biological samples contained therein. According to certain related embodiments, therefore, the biological sample storage device comprises at least one radio frequency transponder device as described herein, which may be an integral component of the storage device and/or may be affixed to an interior or exterior surface of the storage device. Additionally or alternatively, the storage device may be barcode labeled, and/or may optionally contain one or more fields for coding using non-erasable marker pens, and/or may optionally include an imprinted handling protocol. The plastic material of the sample plate may be about 1/10 of a mm to about 2 mm thick, transmits heat instantly, and is heat resistant up to about 100° C.

The sample plate contains holding areas or wells with a footprint that is preferably round in shape but can also be square, rectangular, oblong, or of any other shape. The bottom portion of the wells can be flat, conical, cylindrical or round in shape or of any other shape. The edges of the wells can be of cylindrical, conical or other shape. The number of wells can be as low as 1 well per sample plate and as many as several thousand. Most preferably there are about 96 to about 384 wells located in the sample plate. The sample wells can also be split into groups of 1, 4, and 8 wells that can be fit into the standard sample plate described here. The wells are arranged on the plates in rows. For the plates with 96 wells one row contains 8 wells. A unique aspect is that the sample plate can be a tray that accepts a number of individual sample slides having a varied plurality of wells. Each slide fits into the tray and allows for the storage of a varied number of wells in a single plate. The lower surface of the wells is thin, preferably with a thickness of about 1/10 of a mm to about 2 mm.

It is contemplated that the present invention will be of major value in high throughput screening; i.e., in automated testing or screening of a large number of biological samples. It has particular value, for example, in screening synthetic or natural product libraries for active compounds. The apparatus and methods of the present invention are therefore amenable to automated, cost-effective high throughput biological sample testing or drug screening and have immediate application in a broad range of pharmaceutical drug development programs. In a preferred embodiment of the invention, the wells are organized in a high throughput screening format such as a 96-well plate format, or other regular two dimensional array, such as a 1536- or 384-well format. For high throughput screening the format is therefore preferably amenable to automation. It is preferred, for example, that an automated apparatus for use according to high throughput screening embodiments of the present invention is under the control of a computer or other programmable controller. The controller can continuously monitor the results of each step of the process, and can automatically alter the testing paradigm in response to those results.

Typically, and in certain preferred embodiments such as for high throughput drug screening, candidate agents are provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. Candidate agents further may be provided as members of a combinatorial library, which preferably includes synthetic agents prepared according to a plurality of predetermined chemical reactions performed in a plurality of reaction vessels, which may be provided as wells in a storage device according to the present disclosure. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694 and PCT/US91/04666) or other compositions that may include small molecules as provided herein (see e.g., PCT/US94/08542, EP 0774464, U.S. Pat. Nos. 5,798,035, 5,789,172, 5,751,629). Those having ordinary skill in the art will appreciate that a diverse assortment of such libraries may be prepared according to established procedures using storage devices as described herein, and/or tested using devices and methods according to the present disclosure. For example, members of a library of test compounds can be administered to a plurality of biological samples in each of a plurality of wells in a sample storage device for use as a high throughput screening array as provided herein.

The wells may accommodate a biological sample or a biological material in the form of either liquid or dry material or both. Solid matrix material, such as but not limited to sponge-like material, silica, silica powder, silica filter paper, absorbent powder, or filter paper or other matrix materials as described herein can be added to the wells and will allow the introduction of biological materials, according to non-limiting theory, by absorption, adsorption, specific or non-specific binding or other mechanism of attachment, including those involving formation of non-covalent and/or covalent chemical bonds and or intermolecular associative interactions such as hydrophobic and/or hydrophilic interactions, hydrogen bond formation, electrostatic interactions, and the like. The matrix material may be integrated in the production process of the sample plate unit, or attached through adhesive interactions or wedged into the wells, or later introduced into the wells, prior to, concomitant with, or subsequent to introduction of one or more biological samples into one or more wells. The rim of the wells may be straight or may contain protruding edges. Protruding edges may in certain embodiments retain the material matrix within the wells with or without adhesive interactions. Liquid storage may be achieved through reverse conical shape of the wells with a small opening on the surface of the bottom plate. A reverse conical shape will retain the liquid within the wells in a spill-proof fashion.

The lid may be either flat or have protrusions that fit into the wells of the bottom sample plate. The lid and the sample plate close either through snug fit of the sample plate and the lid, or provide an airtight closure joint or a cushion of compressible material. The joint may either be placed around the perimeter of the sample plate and lid or around each single well. The joint may be attached to the sample plate or to the lid. Preferably, the joint is located in a rim, or glued to the lid using an adhesive material. An airtight fit may be achieved by inserting the protrusions from the lid as a precision seal into the sample plate wells.

The sample plate may be connected to the lid through a hinge system, located on one of the sides of the storage unit, but it may also be located on the two opposite sides. The hinge connects the two units and allows the opening and closing of the storage unit. The device may be produced out of plastic material, whereas the type of plastic can be determined dependent on its application. The hinge or hinges allow for removal of the lid from the sample plate.

The closure of the lid and the sample plate for the long-term storage of biological material may in certain preferred embodiments be achieved through magnetic adhesion, although other means for closing the lid onto the plate may also be employed according to other embodiments contemplated according to the present disclosure, including, as non-limiting examples, snaps, seals, adhesives, hooks-and-loops, threading closures, solenoids, frustroconical closures, bayonets, pinch closures, clasps, and the like, or other closure means. The sample plate and the lid of the storage unit thus, in preferred embodiment, contain magnets that may be in the form of a magnetic sheet or in the form of small magnets located within the sample plate and lid of the storage device. The magnetic attraction between the sample plate and lid is strong enough to allow the tight seal of the storage plate but not so strong as to prevent easy of opening, or twisting or deforming of the sample plate when the lid is opened. The magnetic closure may be used to attach other devices to the storage unit that allows the processing of biological material prior to deposition into the storage unit. The magnetic attraction of the storage unit may be used to attach the storage device to additional devices below the unit. The magnetism is the connecting mechanism of the basic unit to other devices or units.

The storage device preferably comprises at least one identification and data storage tag such as a radio frequency transponder device or "RF tag", for use as part of a radio frequency communication interface between the biological sample storage device and the computer-implemented systems described herein. Certain embodiments contemplate inclusion of a plurality of RF tags within or on the storage device. The storage device may also, according to certain embodiments, comprise visual recognition parts. The different wells may, for instance, be numbered and marked through the engraving of numbers and letters onto the sample plate or through application of a printing process. Optionally, at least one side of the sample plate may have a barcode attached or engraved on its surface. The lid of the storage device may have an area for written notes and comments of any kind. In addition, the upper surface of the lid may also have a barcode, duplicating the barcode of the sample plate. Dual barcoding allows for the unique identification of the biological material and for the association of the sample plate and the lid. Multiple RF tags and/or multiple barcoding sites may provide a security mechanism in case one of these identification/data storage devices becomes detached, damaged or otherwise unreadable.

The Dry Storage Device

The dry storage device is an application of the storage device as described in this invention, which contains treated matrix material for use as a dry storage matrix material such as but not limited to sponge-like material, silica, silica powder, silica filter paper, absorbent powder, cotton, wool, linen, polyester or filter paper, and also including a matrix material that dissolves or dissociates as described herein, for long-term storage of a biological sample or a biological material, such as but not limited to blood, bacteria, cells, viruses, chemical compounds (whether naturally occurring or artificially produced), plasmid DNA, DNA fragments, oligonucleotides, peptides, fluorogenic substrates, genomic DNA, PCR products, cloned DNA, proteins, RNA, minerals or chemicals. These and related embodiments derive from the surprising observation that stable, long-term dry storage of biological samples or biological materials may be effected without refrigeration when such samples or materials are loaded onto a suitable matrix material such as those described herein, including a dissolvable (or dissociable) matrix material. Accordingly, the present invention provides devices for stable, long-term dry storage of biological samples at common indoor ambient room temperatures (e.g., typically 20-27° C. but varying as a function of geography, season and physical plant from about 15-19° C. to about 28-32° C.) for use in the sample data processing methods and systems described herein.

In preferred embodiments that employ the dry storage device, sample loading results in dry storage, for example, whereby a liquid sample is absorbed by, adsorbed to or otherwise entrapped by the matrix material such that after loading no free liquid is readily discernible in or on, or easily dislodged from, the matrix material, and which may in certain other embodiments be a dissolvable matrix material or a dissociable matrix material that may be dried before, during, or after being contacted with the sample to provide dry storage. Related preferred embodiments thus involve the use of sample storage devices as described herein that comprise a matrix material which is capable of dry storage of a biological sample or a biological material without refrigeration, for example, at ambient room temperature. In certain related embodiments a drying step may be performed to effect loading of the sample onto the matrix material for dry storage, for example by air drying, drying at elevated temperature or by the volatilization of solvent through exposure of the sample loaded matrix material to reduced atmospheric pressure (e.g., lyophilization or other vacuum drying method) or to a gentle flowstream of a compatible gas such as nitrogen. The samples are preferably stored dry under conditions that stabilize the sample, i.e., little or no detectable (e.g., with statistical significance) degradation or undesirable chemical or physical modification of the sample occurs, according to criteria that will vary as a factor of the nature of the sample being stored and that will in any event be familiar to those having skill in the relevant art.

Certain embodiments provide compositions and methods for storing biological material (genomic DNA, plasmid DNA, DNA fragments, RNA, oligonucleotides, proteins, peptides, fluorogenic substances, cells, viruses, chemical compounds, etc.) on a matrix comprised of a material that dissolves or dissociates in a solvent that allows complete recovery or substantial recovery (e.g., recovery of at least 50 percent, preferably at least 60 percent, more preferably at least 70 percent, more preferably at least 80 percent, and typically in more preferred embodiments at least 85 percent, more preferably at least 90 percent, more preferably at least 95 percent, still more preferably greater than 97, 98 or 99 percent) of the dried sample material after hydration, rehydration or other solvent reconstitution of the sample. For example, a dissolvable matrix may be capable of being solubilized in a suitable solvent that can be selected based on the properties of the matrix material and/or of the sample depending on the particular methodology being employed and in a manner that permits recovery of one or more desired structural or functional properties of the sample (e.g., biological activity). Similarly, as another example, the matrix material may dissociate in a solvent and may, but need not, become fully solubilized, such that a dispersion, suspension, colloid, gel, sap, slurry, syrup, or the like may be obtained.

In certain of these and related embodiments, the first solvent which is used to introduce the matrix material and/or the biological sample to the biological sample storage device prior to a drying step for dry sample storage may be the same as the second solvent that is subsequently used to hydrate, rehydrate, reconstitute or resuspend the dried sample/matrix combination, and in other embodiments the second solvent may be different from the first. Criteria for selection of a suitable solvent for dissolving or dissociating the matrix material and/or the biological sample will be known to those familiar with the relevant art based, for example, on physicochemical properties of the particular matrix material and sample being used, and on the structural or functional properties (e.g., bioactivity) that are desirably retained during dry storage and subsequent reconstitution, as well as on other factors (e.g., compatibility with other storage device materials, or liquid handling equipment, safety, etc.). Solvents may be selected, for instance, based on the solvent polarity/polarizability (SPP) scale value using the system of Catalan et al. (e.g., 1995 *Liebigs Ann.* 241; see also. Catalan, 2001 *In: Handbook of Solvents*, Wypych (Ed.), Andrew Publ., NY, and references cited therein), according to which, for example, water has a SPP value of 0.962, toluene a SPP value of 0.655, and 2-propanol a SPP value of 0.848. Methods for determining the SPP value of a solvent based on ultraviolet measurements of the 2-N,N-dimethyl-7-nitrofluorene/2-fluoro-7-nitrofluorene probe/homomorph pair have been described (Catalan et al., 1995). Solvents with desired SPP values (whether as pure single-component solvents or as solvent mixtures of two, three, four or more solvents; for solvent miscibility see, e.g., Godfrey 1972 *Chem. Technol.* 2:359) based on the solubility properties of a particular matrix material can be readily identified by those having familiarity with the art in view of the instant disclosure.

According to non-limiting theory, the dissolvable or dissociable matrix material may therefore be a polymer structure that, by forming a matrix, creates a three dimensional space which allows biological material of the biological sample to associate with the matrix. The dissolvable or dissociable matrix material may be used to introduce stabilizing agents such as salts and buffers under dehydrated (e.g., dried or substantially solvent-free) conditions. The matrix also allows the adjustment of pH and other parameters for optimal drying and storage conditions, and may comprise one or a plurality of detectable indicators as provided herein, such as color-based pH indicators, and/or moisture indicators. In certain preferred embodiments the matrix material comprises polyvinyl alcohol (PVA), a dissolvable matrix material.

According to certain other embodiments, the dissolvable or dissociable matrix material may be any suitable material having the compatible characteristics for storing a particular type of biological sample in a manner that satisfactorily preserves the desired structural and/or functional properties, said characteristics including the ability to dry in a manner that forms a matrix within the interstices of which the biological molecules of interest are deposited, and also including appropriate solvent (e.g., biological buffer) compatibility further including an ability to be redissolved or resuspended subsequent to dry storage in a manner whereby the matrix molecules do not interfere with one or more biological activities of interest in the sample. Additional non-limiting examples of a matrix material that dissolves or dissociates in a solvent include polyethylene glycol, agarose, poly-N-vinylacetamide, polyvinylpyrrolidone, poly(4-vinylpyridine), polyphenylene oxide, reversibly crosslinked acrylamide, polymethacrylate, carbon nanotubes (e.g., Dyke et al., 2003 *JACS* 125:1156; Mitchell et al., 2002 *Macromolecules* 35:8825; Dagani, 2003 *C&EN* 81:5), polylactide, lactide/glycolide copolymer, hydroxymethacrylate copolymer, calcium pectinate, hydroxypropyl methylcellulose acetate succinate (e.g., Langer, 1990 *Science* 249:1527; Langer, 1993 *Accounts Chem. Res.* 26:537-542), heparin sulfate proteoglycan, hyaluronic acid, glucuronic acid (e.g., Kirn-Safran et al., 2004 *Birth Defects. Res. C. Embryo Today* 72:69-88), thrombospondin-1 N-terminal heparin-binding domain (e.g., Elzie et al., 2004 *Int. S. Biochem. Cell Biol.* 36:1090; Pavlov et al., 2004 *Birth Defects Res. C. Embryo Today* 72:12-24), fibronectin (e.g., Wierzbicka-Patynowski et al., 2003 J Cell Sci. 116(Pt 16):3269-76), a peptide/water-soluble polymeric modifier conjugate (e.g., Yamamoto et al., 2002 *Curr Drug Targets* 3(2):123-30), and collagen or collagen fragments including basement membrane collagen peptides (e.g., Ortega et al., 2002 *J Cell Sci.* 115(Pt 22):4201-14).

Other detectable indicators include compositions that permit detection (e.g., with statistical significance relative to an appropriate control, as will be know to the skilled artisan) or similar determination of any detectable parameter that directly relates to a condition, process, pathway, induction, activation, inhibition, regulation, dynamic structure, state, contamination, degradation or other activity or functional or structural change in a biological sample, including but not limited to altered enzymatic (including proteolytic and/or nucleolytic), respiratory, metabolic, catabolic, binding, catalytic, allosteric, conformational, or other biochemical or biophysical activity in the biological sample, and also including interactions between intermediates that may be formed as the result of such activities, including metabolites, catabolites, substrates, precursors, cofactors and the like.

A wide variety of detectable indicators are known to the art and can be selected for inclusion in the presently disclosed compositions and methods depending on the particular parameter or parameters that may be of interest for particular biological samples in particular sample storage applications. Non-limiting examples of parameters that may be detected by such detectable indicators include detection of the presence of one or more of an amine, an alcohol, an aldehyde, water, a thiol, a sulfide, a nitrite, avidin, biotin, an immunoglobulin, an oligosaccharide, a nucleic acid, a polypeptide, an enzyme, a cytoskeletal protein, a reactive oxygen species, a metal ion, pH, $Na^+$, $K^+$, $Cl^-$, a cyanide, a phosphate, selenium, a protease, a nuclease, a kinase, a phosphatase, a glycosidase and a microbial contaminant, and others.

Examples of a broad range of detectable indicators (including calorimetric indicators) that may be selected for specific purposes are described in Haugland, 2002 *Handbook of Fluorescent Probes and Research Products—Ninth Ed.*, Molecular Probes, Eugene, Oreg.; in Mohr, 1999 *J. Mater. Chem.*, 9: 2259-2264; in Suslick et al., 2004 *Tetrahedron* 60:11133-11138; and in U.S. Pat. No. 6,323,039. (See also, e.g., Fluka Laboratory Products Catalog, 2001 Fluka, Milwaukee, Wis.; and Sigma Life Sciences Research Catalog, 2000, Sigma, St. Louis, Mo.) A detectable indicator may be a fluorescent indicator, a luminescent indicator, a phosphorescent indicator, a radiometric indicator, a dye, an enzyme, a substrate of an enzyme, an energy transfer molecule, or an affinity label. In certain preferred embodiments the detectable indicator may be one or more of phenol red, ethidium bromide, a DNA polymerase, a restriction endonuclease (e.g., a restriction enzyme used as a restriction nuclease such as a site- or sequence-specific restriction endonuclease), cobalt chloride (a moisture indicator that changes from blue color when water is present to pink when dry), Reichardt's dye (Aldrich Chemical) and a fluorogenic protease substrate.

A detectable indicator in certain embodiments may comprise a polynucleotide polymerase and/or a suitable oligonucleotide, either or both of which may be employed as an indicator or, in certain other embodiments, as components of other nucleic acids-based applications of the compositions and methods described herein. Polymerases (including DNA polymerases and RNA polymerases) useful in accordance with certain embodiments of the present invention include, but are not limited to, *Thermus thermophilus* (Tth). DNA polymerase, *Thermus aquaticus* (Taq) DNA polymerase, *Thermologa neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants; variants and derivatives thereof may also be used in accordance with the invention.

Polymerases used in accordance with the invention may be any enzyme that can synthesize a nucleic acid molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; 5,512,462; WO 92/06188; WO 92/06200; WO 96/10640; Barnes, W. M., *Gene* 112:29-35 (1992); Lawyer et al., *PCR Meth. Appl.* 2:275-287 (1993); Flaman et al., *Nucl. Acids Res.* 22(15): 3259-3260 (1994)).

Other detectable indicators for use in certain embodiments contemplated herein include affinity reagents such as antibodies, lectins, immunoglobulin Fc receptor proteins (e.g., *Staphylococcus aureas* protein A, protein G or other Fc receptors), avidin, biotin, other ligands, receptors or counterreceptors or their analogues or mimetics, and the like. For such affinity methodologies, reagents for immunometric measurements, such as suitably labeled antibodies or lectins, may be prepared including, for example, those labeled with radionuclides, with fluorophores, with affinity tags, with biotin or biotin mimetic sequences or those prepared as antibody-enzyme conjugates (see, e.g., Weir, D. M., *Handbook of Experimental Immunology*, 1986, Blackwell Scientific, Boston; Scouten, W. H., *Methods in Enzymology* 135:30-65, 1987; Harlow and Lane, *Antibodies: A Laboratory Manual*, Cold Spring Harbor Laboratory, 1988; Haugland, 2002 *Handbook of Fluorescent Probes and Research Products— Ninth Ed.*, Molecular Probes, Eugene, Oreg.; Scopes, R. K., *Protein Purification: Principles and Practice*, 1987, Springer-Verlag, NY; Hermanson, G. T. et al., *Immobilized Affinity Ligand Techniques*, 1992, Academic Press, Inc., NY; Luo et al., 1998 *J. Biotechnol.* 65:225 and references cited therein).

The dissolvable (or dissociable) matrix may be applied to storage containers for biological samples, for example, by contacting or administering a matrix material that dissolves or dissociates in a solvent to one or a plurality of sample wells of a storage device as described herein. For instance, the dissolvable matrix material may readily adhere to tubes and plates made of glass or plastic such as polypropylene, polystyrene or other materials. The dissolvable material is dried, which may by way of non-limiting illustration be accomplished by air drying at ambient temperature (typically within the range 20° C.-30° C. such as at 22° C., 23° C., 24° C., 25° C.) and/or at an appropriately elevated temperature, and/or under reduced atmospheric pressure (e.g., partial or full vacuum) and/or under a suitable gas stream such as a stream of filtered air, $CO_2$ or an inert gas such as nitrogen or other suitable drying gas, or by other drying means. After the step of drying, which may be complete drying (e.g., with statistical significance, all or substantially all detectable solvent has been removed) or partial drying, the dissolvable/dissociable matrix material is ready to accept the biological sample to be stored.

Biological material provided in or derived from a biological sample may also be added to the wells or tubes in combination with the storage matrix in liquid form (e.g., by simultaneously contacting the sample well with the sample and the matrix dissolved or dissociated in a solvent), allowing the drying of the biological material and the matrix material to proceed at the same time. The dissolvable matrix does not, in preferred embodiments, interfere with biochemical reactions such that purification steps may not be required to separate the matrix from the biological sample prior to further processing of the sample, for instance, prior to performance of biochemical reactions, such as assays or the like, in the wells of the sample storage device.

The buffer conditions in the dissolvable matrix may be adjusted such that greater than at least 90 percent, preferably greater than 95 percent, more preferably greater than 96, 97, 98 or 99 percent of the biological activity (e.g., enzymatic or affinity activity, or structural integrity or other biological activity as described herein and known to the art) of the biological sample is maintained upon solvent reconstitution (e.g., rehydration with water), eliminating the need to laboriously remove the sample from the storage container and transfer it to a reaction buffer in a separate container. Certain such invention embodiments correspondingly provide the unexpected advantage of eliminating the need to separately aliquot and/or calibrate certain biological reagents each time a stored sample is to be assayed.

The dissolvable/dissociable matrix may also be prepared in the sample storage device in a manner such that one or more wells contain at least one inhibitor that is a biological inhibitor or a biochemical inhibitor, where such inhibitors include any agent that may desirably be included to preserve, stabilize, maintain, protect or otherwise contribute to the recovery from the biological sample storage device of a biological sample that has substantially the same biological activity as was present prior to the step of contacting the sample with the sample storage device. Accordingly, in certain preferred embodiments the biological sample storage device comprises at least one inhibitor, for example, an anti-microbial agent such as (but not limited to) an anti-fungal and/or antibacterial agent capable of suppressing bacterial or fungal growth to inhibit microbial contamination of the wells and the stored sample during longterm storage.

In certain related embodiments the inhibitor may be a reducing agent, an alkylating agent, an antimicrobial agent, a kinase inhibitor, a phosphatase inhibitor, a caspase inhibitor, a granzyme inhibitor, a cell adhesion inhibitor, a cell division inhibitor, a cell cycle inhibitor, a lipid signaling inhibitor and/or a protease inhibitor. Those familiar with the art will be aware of a wide range of readily available inhibitors that may be selected depending on the nature of the biological sample and the particular bioactivity of interest. See, e.g., Calbiochem® Inhibitor SourceBook™ (2004, EMD Biosciences, La Jolla, Calif.). For antimicrobial agents, see, e.g., Pickering, L K, Ed. 2003 *Red Book: Report of the Committee on Infectious Diseases*, 26th edition. Elk Grove Village, IL, pp. 695-97.; American Academy of Pediatrics, 1998, *Pediatrics*, 101(1), supplement; *Disinfection Sterilization and Preservation*, Seymour S. Block (Ed.), 2001 Lippincott Williams & Wilkins, Philadelphia; *Antimicrobial Inhibitors*, A. I. Laskin and H. A. Lechevalier, (Eds.), 1988 CRC Press, Boca Raton, Fla.; *Principles and Practice of Disinfection, Preservation and Sterilization*, A. D. Russell et al., (Eds.), 1999, Blackwell Science, Malden, MA; *Antimicrobial/anti-infective materials*, S. P. Sawan et al., (Eds.), 2000 Technomic Pub. Co., Lancaster, PA; *Development of novel, antimicrobial agents: emerging strategies*, K. Lohner, (Ed.), 2001 Wymondham, Norfolk, UK; Conte, J. E. *Manual of antibiotics and infectious diseases* (9th Ed.), 2001, Lippincott Williams & Wilkins, Philadelphia.

In certain embodiments the inhibitor may be the fungizide validamycin A (Research Products International Corp., Mt. Prospect, IL, catalog no. V21020), the protease inhibitor TL-3 (Lee et al., 1998 *Proc. Nat. Acad. Sci. USA* 95:939; Lee et al., 1999 *J. Amer. Chem. Soc.* 121:1145; Buhler et al., 2001 *J. Virol.* 75:9502), sodium orthovanadate, sodium fluoride, N-α-tosyl-Phe-chloromethylketone, N-α-tosyl-Lys-chloromethylketone, aprotinin, phenylmethylsulfonyl fluoride or diisopropylfluoro-phosphate.

As described herein, an added advantage of the dissolvable matrix is that the storage container can be directly used as a reaction chamber after dissolving the matrix and rehydration of the material. The stability and activity of proteins in liquid form may be dependent on activity requirements such as pH, salt concentration, and cofactors. The stability of many proteins may in some cases be extremely labile at higher temperatures and the drying of proteins at ambient (e.g., room) temperature may therefore provide a stabilizing environment.

As also described herein in the Examples, the presence of trehalose, believed to contribute to the stabilization of biological samples (e.g., Garcia de Castro et al., 2000 *Appl. Environ. Microbiol.* 66:4142; Manzanera et al., 2002 *Appl. Environ. Microbiol.* 68:4328), was not sufficient under certain conditions to support recovery of enzymatic activity in a protein following dry storage. As a brief background, trehalose is the natural substrate of trehalase, an enzyme that cleaves disaccharides. Trehalose is known to stabilize organic material such as proteins, but when present under suboptimal conditions may be disadvantageous for longterm storage of proteins at ambient temperatures, since it is a natural energy source for fungi and bacteria. Contamination with bacteria or fungi of a biological sample stored in the presence of trehalose at less than optimal dry storage conditions will result in growth of the microbe(s), and undesirable microbial contamination of the stored sample can result. Validamycin is a trehalase inhibitor having a slightly different chemical structure than that of trehalose. Validamycin is a non-toxic fungicide that inhibits fungal growth by blocking the enzyme activity of trehalase. Surprisingly and as disclosed herein and in the Examples, validamycin A is able to stabilize biological material at ambient temperatures. In addition to the protective effect for long-term storage of biological material, validamycin also protects the stored sample from contamination from microorganisms.

Accordingly, certain embodiments of the invention expressly contemplate a biological sample storage device that does not include trehalose as a component of a sample well or of a matrix material, and similarly certain embodiments may expressly exclude from the sample well or matrix material the presence of polystyrene and/or of hydroxyectoine. In view, however, of the unexpected advantages disclosed herein as they relate to the inclusion of validamycin (e.g., validamycin A) as an inhibitor in biological sample storage devices, certain other embodiments contemplated herein may include any one or more of trehalose, hydroxyectoine, and/or polystyrene. According to non-limiting theory, validamycin A, a trehalase inhibitor known to the agricultural art as a fungicide, provides a surprising stabilizing effect when used in combination with a dissolvable matrix in the biological sample storage devices, as disclosed herein. Alternatively or additionally to the use disclosed herein of validamycin along with the dissolvable matrix, other small molecules that have activity as inhibitors or activators of trehalase may be usefully included in the storage devices, as inhibitors or as additives to the matrix material and/or to the sample, including natural disaccharides, pseudo-sugars that are also known as carba-sugars, and/or other inhibitors/activators of trehalase. In addition, validamycin provides an advantage according to certain embodiments disclosed herein, in that it protects the longterm storage media from fungal, bacterial or other types of contamination.

Other non-limiting examples of matrix materials that may be used as dry storage matrix materials include materials that comprise one or more of polycarbonate, cellulose (e.g., cellulose papers such as FTA™ paper, Whatman Corp., Florham Park, N.J.), cellulose acetate, cellulose nitrate, nitrocellulose, agarose, crosslinked agarose such as 2,3-dibromopropanol-crosslinked agarose, 3,6-anhydro-L-galactose, dextrans and other polysaccharides including chemically crosslinked polysaccharides such as epichlorohydrin-crosslinked dextran or N,N'-methylene bisacrylamide-crosslinked dextran, borosilicate microfiber glass, fiberglass, asbestos, polymers and plastics such as polypropylene, polystyrene, polyvinylidene fluoride (PVDF), nylon, polysulfone, polyethersulfone, polytetrafluoroethylene, and derivatives of these materials (e.g., U.S. Pat. No. 5,496,562) as well as other similar materials as are known in the art, or as can readily be determined to be suitable for use in the devices and methods described herein based on the present disclosure. See also, for example, U.S. Pat. Nos. 5,089,407, 4,891,319, 4,806,343, and 6,610,531.

The matrix material may be treated for the storage and preservation of biological materials. It is well documented that the adjustment of buffer conditions and the addition of chemicals and enzymes and other reagents can stabilize DNA and RNA (for example, Sambrook et al., 1989; Current Protocols, Nucleic Acid Chemistry, Molecular Biology, Wiley and Sons, 2003) and proteins and other biological materials (for example, blood, tissue, bodily fluids) against degradation from enzymes, proteases and environmental factors (for example, Current Protocols, Protein Sciences, Cell Biology, Wiley and Sons, 2003). A method that combines certain chemical components and beneficial effects may be applied. Various chemical components may include but are not limited to sodium dodecyl sulfate (SDS), diethyl pyrocarbonate, Tris buffer, Tris-EDTA buffer (TE), sodium chloride/sodium citrate buffer (SSC), MOPS/sodium acetate/EDTA buffer (MOPS), ethylenediamine tetraacetic acid (EDTA), sodium acetate buffer at physiological pH, Guanidinium thiocyanate, ethylenediamine tetraacetic acid (EDTA), human placental ribonuclease inhibitor, a bovine ribonuclease inhibitor, a porcine ribonuclease inhibitor, diethyl pyrocarbonate, ethanol, formamide, guanidinium thiocyanate, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol or specific inhibiting antibodies.

Each well holds about 5 µl to about 100 µl of liquid sample material, preferably about 10 µl to about 30 µl of liquid sample material. Sample amounts can vary from about 0.01 µg to about 1000 µg of DNA, RNA, protein, blood, urine, virus, bacteria, cells, tissue, cell extract, tissue extract, metabolites, chemicals, or other materials. Sample application is through direct spotting and can be automated. The spotted wells may be provided with a color indicator that changes color indicating an occupied well. Color change may be achieved by adding a color agent. For example, ponco red dye, Nitrazine yellow, Brom Thymol Blue, Bromocresol Green, Methyl Orange, Congo red, Bromochlorophenol can be deposited with or prior to subsequent to the sample material, or by treating the matrix material before or after deposition of sample material into the well. A pH-dependent color reagent can be applied that changes color after deposition of a sample with a biological pH of 6.5 to 8.5 onto the matrix within the well. Spotted wells dry within about 1 to about 20 minutes at ambient temperature or within about 0.1 to about 10 minutes at elevated temperature. DNA can be retrieved through re-hydration of the well for up to about 50 to about 80 times. The re-hydration reagent may be a solution or sample buffer with a biological pH of 6.5-8.5. Tris buffer, Tris-EDTA buffer (TE), sodium chloride/sodium citrate buffer (SSC), MOPS/sodium acetate/EDTA buffer (MOPS, sodium acetate buffer. The dry storage device design is applicable without further modifications for the storage of purified genomic DNA from bacterial, yeast, human, animals, plants and other sources. With additional modification, such as but not limited to coating the filters with denaturing agents for proteases, the dry storage device can be also used for bacteria, buccal swabs, biopsy tissue, semen, urine, blood, proteins and other samples.

Related embodiments are directed to kits that comprise the biological sample storage device as described herein, along with one or more ancillary reagents that may be selected for desired uses. Optionally the kit may also include a box, case, jar, drum, drawer, cabinet, carton, carrier, handle, rack, tray, pan, tank, bag, envelope, sleeve, housing or the like, such as any other suitable container. Ancillary reagents may include one or more solvents or buffers as described herein and known to the art, and may in certain embodiments include an activity buffer.

An activity buffer may comprise a solvent or solution in liquid form, including a concentrate, or one or more dry ingredients which, when reconstituted with, dissolved in and/or diluted with one or more appropriate solvents (e.g., water typically, or alternatively, an alcohol such as methanol, ethanol, n-propanol, isopropanol, butanol, etc., an organic solvent such as dimethylsulfoxide, acetonitrile, phenol, chloroform, etc. or other solvent) as appropriate for the intended use, results in a liquid that is suitable for a desired use of the biological sample, such as a functional or structural characterization of one or more components of the sample.

Non-limiting examples of such uses may include determining one or more enzyme activities, determining intermolecular binding interactions, detecting the presence of a specific polynucleotide or amino acid sequence or of an immunologically defined epitope or of a defined oligosaccharide structure, detection of particular viruses or of microbial cells or of human or animal cells, determining particular metabolites or catabolites, etc., all of which can be accomplished using conditions that are defined and known to those skilled in the relevant art, including suitable conditions that can be provided through contacting the sample with an appropriate activity buffer.

The Wet Storage Device

The storage device can be modified for wet storage of samples through one or more changes to the well design. Cross-contamination across wells through spillage while opening and closing of the wells is avoided by a design that provides a small opening on the top part of the well while retaining the liquid in the well through surface tension.

The small opening on the top part of the well may be provided through a reverse cone design or through plastic flaps protruding from the top of the well into the open space reducing the overall opening of each well. The wet storage device is manufactured by injection molding and can be made in one piece or in two pieces similar to the storage device. The wet storage device withstands temperatures ranging from about −80° C. to about 100° C.

Strip Well Module

All devices and applications described in this invention may be used in a strip well format with either 1, 4 or 8 well strips. The strip well module has the same or similar basic footprint as the storage device. It allows the storage of smaller sample numbers than the 96 well plate unit. The modular design allows the attachment of well strips to a thin base platform. One strip can either contain 1, 4 or 8 wells. The strips can be attached to a thin base-plate either through magnetic interactions or through clips present at the end of the strips The height of one strip, including the thickness of the base-plate, is equal to a regular basic storage unit, so that the lid of the unit allows for the closing of the device.

The Pressure Device

The Pressure Device of the present invention is comprised of several modules, which include the previously described sample storage device, a filter unit, a pressure plate unit, and a pressurized air system. All units are of equal dimension, equivalent to a standard 96-well, 384-well or 1535-well biological sample plate. The dimensions of the pressure device are about 2 mm to about 25 mm in height, 80 mm to 200 mm in length, and about 60 mm to about 150 mm in width. Preferably, the pressure device has a height of about 3 mm to about 20 mm, a length of about 100 mm to about 140 mm, and a width of about 60 mm to about 100 mm, but can also have smaller dimensions to accommodate small sample numbers, or smaller sample systems. All modules may vary in dimension dependent on the size of the sample storage device dimension, whereas the number of wells can be as low as 1 well per sample plate and as many as tens of thousands. Most preferably 96 or 384 wells may be provided in the sample plate and processed through each of the pressure plate units. The number of sample wells of each pressure device can also be split into groups of 1, 4 and 8 wells that can be fit into the standard sample device described in this invention. The pressure device is made out of colorful plastic material or out of, metal or of combinations of both. The body of the pressure device and its modules is made by injection molding or machine tooling or a combination of both.

The filter unit may be attached to the pressure device and the sample storage device and any other devices described herein by magnetic forces. An additional clasp may be provided to aid in withstanding air pressure during operation. The filter unit may be made out of colorful solid material such as polypropylene, acrylic, and contains paper or a solid matrix for filtration. Preferably, the filter unit has a thickness of about 1 mm to about 15 mm depending on the substrate used for filtration. The filter unit has the appropriate number of holes/slots that fit over a sample storage device and holds 96, 384, 1536 or more sample deposit holes. Each filter unit has its own tight sealing lid. The rim of the holes can be either straight or can contain protruding edges. Protruding edges can retain the matrix material within the holes with or without adhesive interactions.

Each hole within the filter unit may contain matrix materials, such as but not limited to sponge-like material, silica, absorbent powder, and filter paper for the filtration of biological materials, such as but not limited to blood, bacteria, genomic DNA, mitochondrial DNA, PCR products, cloned DNA, proteins, RNA, proteins, minerals or chemicals. The matrices may be selected to support biological sample processing, for example by way of illustration and not limitation, one or more of DNA purification, PCR amplification, sample size fractionation (e.g., on the basis of molecular size or cell size), serum processing, blood processing, protein purification and cell sorting. The matrix materials may be either integrated in the production process of the sample plate unit, or attached through adhesive interactions or wedged into the holes. The matrices are prepared using standard technology necessary to make size fractionation filters, or treated material to degrade or retain unwanted biological fractions (for example, Current Protocols, Molecular Biology, Wiley and Sons, 2003). The matrix materials may also be treated with antibodies, lectins, or other affinity, charge-selective, ion selective, group selective (e.g., amino or carboxyl functionalities), hydrophobic, hydrophilic or other selectivity molecules or the like to retain fractions of the sample material, and/or with small chemical entities conferring desired biological or chemical functions or functionalities (see, for example, Current Protocols in Molecular Biology, John Wiley and Sons, 2003; Scopes, R. K., *Protein Purification: Principles and Practice*, 1987, Springer-Verlag, NY; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California). The matrix materials may be pretreated to preserve the biological material by regulation of buffer conditions and by modification of chemical additives, stabilizers or degradation reagents (for example, Sambrook et al., 1989; Current Protocols, Nucleic Acid Chemistry, Protein Science, Molecular Biology, Cell Biology, Wiley and Sons, 2003). Each hole may process from about 5 µl to about 1000 µl of sample volume. Sample amounts can vary from about 0.1 µg of DNA to about 1000 µg of DNA, RNA, protein, blood, urine, virus, bacteria, cells, tissue, cell extract, tissue extract, metabolites, chemicals, or other materials. Sample application is through direct spotting and can be automated.

The pressure plate unit applies air pressure from the top to the filter unit holes and forces the sample through the matrices into the well of the storage device located below. Pressure may be applied from a pressurized laboratory air system or a pressurized air canister. The pressure unit may be applied to introduce through top pressure the reagents into the wells of the sample storage device, the PCR device, the sequencing device, the restriction analysis device, the protein crystallography device, the diagnostic device, and the strip well device. The pressure plate unit is provided with holes connecting all holes to an air intake. The air intake is attached to a valve that has an air-tight seal connecting the pressure plate unit to a pressurized air source. The pressure unit attaches to an air source by turning and securing the valve. The valve can also be attached to a pressure gauge indicating the required pressure for each specific filter unit.

All modules for the pressure device described herein are preferably airtight to attain a seal that withstands the pressure required to force the sample through the filter system into the storage wells. Each module may be flat or have protrusions that fit exactly into the adjoining module. An airtight fit is created by use of a joint or a cushion of compressible material. The joint may either be placed around the perimeter of each unit or around each single well. Preferably the joint is located in a rim, or affixed to the lid using an adhesive material. An airtight fit may be achieved by inserting the protrusions from each unit as a precision seal into the unit it will be attached to below.

The attachment of all modules, including a pressure unit, a filter unit and a storage device, is preferably achieved through magnetic adhesion (but may alternatively, in these and other device embodiments which follow, employ other closure means as described herein). Each unit contains magnets either in the form of a magnetic sheet or in the form of small magnets. The magnetic attraction between each unit is strong enough to allow the tight seal for the processing of biological material prior to deposition into the sample storage or other device. The magnetic attachment of the three independent modules (pressure unit, filter unit and storage device) may be further secured by clasps. The clasps may be made of metal or plastic material that is formed to wedge the three modules together and to reinforce the magnetic attachment mechanism. The clasp preferably has dimensions smaller than the sides of the filtration unit. The clasps may be attached through the application of outside pressure that opens the clasp, or the clasps may be designed to slide over the outside of the filter module. Two or more clasps may be utilized to secure the filter unit.

Each module has visual recognition parts. The different wells may numbered and marked through the engraving of numbers and letters onto the sample plate or through application of a printing process.

Portable PCR Device

The sample plate may be attached to a thermocycling unit (PCR device) through magnetic forces. The sample plate and the PCR device contain magnets either in the form of a magnetic sheet or in the form of small magnets located inside of the sample plate. The magnetic attraction between the sample plate and the PCR device allows for exact placement and tight attachment of the sample plate to the PCR device.

The PCR device contains a temperature platform with the footprint of the storage device. The PCR device produces temperatures in the range from about 4° C. to about 100° C. The PCR device contains a computer component that can be programmed for repeated cycling protocols that contain multiple temperatures, varied temperature holding times, and multiple temperature changes that can range from 4° C. to 100° C. and that accommodate the requirements for standard and hot-start PCR amplification conditions (for example, Qiagen "Taq PCR Handbook", Qiagen "Critical Factors for Successful PCR"). The PCR unit can contain an integrated heated lid or cover that sustains and produces constant temperatures up to about 100° C. The lid or cover may be made out of metal or similar material and is placed and held in place via magnetic force on the top of the sample plate. The energy provided for this PCR unit can come from a standard 110/220V electrical outlet, from a battery pack or from a solar driven energy source.

PCR Reagent Module

The PCR reagent module contains all reagents necessary for PCR amplification. It can include reagents such as but not limited to buffers, primers, polymerase enzyme, and deoxynucleotides (for example, Qiagen "Taq PCR Handbook", Qiagen "Critical Factors for Successful PCR"). The reagents are provided in a 96, 384, or 1536 well or larger format which matches the format and dimensions of the sample plate. The dimensions of the PCR reagent module are about 2 mm to about 25 mm in height, about 80 mm to about 200 mm in length, and about 60 mm to about 150 mm in width. Preferably, the PCR reagent module has a height of about 3 mm to about 15 mm, a length of about 100 mm to about 140 mm, and a width of about 60 mm to about 100 mm. The PCR reagent module is made out of colorful polypropylene and holds 96, 384, 1536 or more sample deposit wells. The PCR reagent module is manufactured by injection molding.

Magnetism is the connecting mechanism of the sample plate to the PCR reagent module. The sample plate and the PCR reagent module contain magnets preferably in the form of a magnetic sheet or in the form of small magnets located inside of the sample plate. The magnetic attraction between the sample plate and the PCR reagent module allows for exact placement and tight attachment of the sample plate to the PCR reagent module.

The PCR reagent module may have different designs. Each sample well may or may not have protruding edges that reach into the wells of the sample plate. It may require application of air pressure applied by the pressure device to transfer the reagents from the PCR reagent module into the sample plate.

Sequencing Reagent Module

The sequencing reagent module contains all reagents necessary for DNA sequencing or DNA cycle sequencing. It can include reagents such as but not limited to buffers, primers, sequencing enzyme, deoxynucleotides and dideoxynucleotides (for example, Nucleic Acid Chemistry, Molecular Biology, Wiley and Sons, 2003). The reagents are provided in a 96, 384, or 1536 well or larger format, which matches the format and dimensions of the sample plate. The dimensions of the sequencing reagent module are about 2 mm to about 25 mm in height, about 80 mm to about 200 mm in length, and about 60 mm to about 150 mm in width. Preferably, the sequencing reagent module has a height of about 3 mm to about 15 mm, a length of about 100 mm to about 140 mm, and a width of about 60 mm to about 100 mm. The sequencing reagent module is made out of colorful polypropylene and holds 96, 384, 1536 or more sample deposit wells. The sequencing reagent module is manufactured by injection molding.

Magnetism is the connecting mechanism of the sample plate to the sequencing reagent module. The sample plate and the sequencing reagent module contain magnets preferably in the form of a magnetic sheet or in the form of small magnets located inside of the sample plate. The magnetic attraction between the sample plate and the sequencing reagent module allows for exact placement and tight attachment of the sample plate to the sequencing reagent module.

The sequencing reagent module may have different designs. Each sample well may or may not have protruding edges that reach into the wells of the sample plate. It may require application of air pressure applied by the pressure device to transfer the reagents from the sequencing reagent module into the sample plate.

Primer Extension Reagent Module

The primer extension reagent module contains all reagents necessary for primer extension. It can include reagents such as but not limited to buffers, primers, polymerase enzyme, deoxynucleotides and dideoxynucleotides (for example, Current Protocols, Nucleic Acid Chemistry, Molecular Biology, Wiley and Sons, 2003). The reagents are provided in a 96, 384, or 1536 well or larger format, which matches the format and dimensions of the sample plate. The dimensions of the primer extension reagent module are about 2 mm to about 25 mm in height, about 80 mm to about 200 mm in length, and about 60 mm to about 150 mm in width. Preferably, the primer extension reagent module has a height of about 3 mm to about 15 mm, a length of about 100 mm to about 140 mm, and a width of about 60 mm to about 100 mm. The primer extension reagent module is made out of colorful polypropylene and holds 96, 384, 1536 or more sample deposit wells. The primer extension reagent module is manufactured by injection molding.

Magnetism is the connecting mechanism of the sample plate to the primer extension reagent module. The sample plate and the primer extension reagent module contain magnets preferably in the form of a magnetic sheet or in the form of small magnets located inside of the sample plate. The magnetic attraction between the sample plate and the primer extension reagent module allows for exact a placement and tight attachment of the sample plate to the primer extension reagent module.

The primer extension reagent module may have different designs. Each sample well may or may not have protruding edges that reach into the wells of the sample plate. It may require application of air pressure applied by the pressure device to transfer the reagents from the primer extension reagent module into the sample plate.

Haplotyping Reagent Module

The haplotyping reagent module contains all reagents necessary for DNA haplotyping. It can include reagents such as but not limited to buffers, primers, sequencing enzyme, deoxynucleotides and dideoxynucleotides (for example, Current Protocols, Nucleic Acid Chemistry, Molecular Biology, Wiley and Sons, 2003). The reagents are provided in a 96, 384, or 1536 well or larger format which matches the format and dimensions of the sample plate. The dimensions of the haplotyping reagent module are about 2 mm to about 25 mm in height, about 80 mm to about 200 mm in length, and about 60 mm to about 150 mm in width. Preferably, the haplotyping reagent module has a height of about 3 mm to about 15 mm, a length of about 100 mm to about 140 mm, and a width of about 60 mm to about 100 mm. The haplotyping reagent module is made out of colorful polypropylene and holds 96, 384, 1536 or more sample deposit wells. The haplotyping reagent module is manufactured by injection molding.

Magnetism is the connecting mechanism of the sample plate to the haplotyping reagent module. The sample plate and the haplotyping reagent module contain magnets preferably in the form of a magnetic sheet or in the form of small magnets located inside of the sample plate. The magnetic attraction between the sample plate and the haplotyping reagent module allows for exact placement and tight attachment of the sample plate to the haplotyping reagent module.

The haplotyping reagent module may have different designs. Each sample well may or may not have protruding edges that reach into the wells of the sample plate. It may require application of air pressure applied by the pressure device to transfer the reagents from the haplotyping reagent module into the sample plate.

Restriction Analysis Reagent Module

The restriction analysis reagent module contains all reagents necessary for DNA restriction analysis. It can include reagents such as but not limited to buffers, restriction enzyme, and salt (for example, Sambrook et al., 1989; Current Protocols, Nucleic Acid Chemistry, Molecular Biology, Wiley and Sons, 2003). The reagents are provided in a 96, 384, or 1536 well or larger format, which matches the format and dimensions of the sample plate. The dimensions of the restriction analysis reagent module are about 2 mm to about 25 mm in height, about 80 mm to about 200 mm in length, and about 60 mm to about 150 mm in width. Preferably, the restriction analysis reagent module has a height of about 3 mm to about 15 mm, a length of about 100 mm to about 140 mm, and a width of about 60 mm to about 100 mm. The restriction analysis reagent module is made out of colorful polypropylene and holds 96, 384, 1536 or more sample deposit wells. The restriction analysis reagent module is manufactured by injection molding.

Magnetism is the connecting mechanism of the sample plate to the restriction analysis reagent module. The sample plate and the restriction analysis reagent module contain magnets preferably in the form of a magnetic sheet or in the form of small magnets located inside of the sample plate. The magnetic attraction between the sample plate and the restriction analysis reagent module allows for exact placement and tight attachment of the sample plate to the restriction analysis reagent module.

The restriction analysis reagent module may have different designs. Each sample well may or may not have protruding edges that reach into the wells of the sample plate. It may require application of air pressure applied by the pressure device to transfer the reagents from the restriction analysis reagent module into the sample plate.

Diagnostic Device

The basic sample storage device may be modified to function as an analytical device used in the detection of hormone levels, physiological conditions, human, animal and plant diseases. The diagnostic device may implement the placing of a cylindrical diagnostic device on top of the sample storage device. The diagnostic device may be produced in two ways: 1) an independent production process and added as the complete device into the sample storage device, or 2) layered as independent units within each well of the sample storage device.

The diagnostic device may contain a zone with at least one specific antibody or specific diagnostic reagent within the device. The reagents may produce a visually detectable reaction when an antibody-antigen complex is formed.

Shipping Sleeve

The shipping sleeve is used to safely transport or mail biological material. The shipping sleeve is designed to hold a sample storage device and an information storage medium, for example a compact disc (CD) containing the information concerning the material. In cases where dangerous or infectious materials are shipped the wells can be sealed with an adhesive film prior to closing of the sample storage device. The shipping sleeve has two parts, the bottom part or sample storage device holder, and the enclosure. The bottom part may be made out of cardboard, plastic or foam material than has the exact footprint of the sample storage device and a software CD or other information storage medium. For shipment or transport of biological material the sample is spotted into the wells of the sample storage device, and the lid is closed and sealed through its magnetic lid-closure. The sample storage device is placed into the tight-fit of the shipping sleeve bottom. The CD may be added.

The size of the sample storage device holder may be determined by the size of the sample storage device it may not be smaller than a sample storage device, but it may be larger than 10 stacked sample storage devices. The surrounding padding material preferably consists of at least about 5 mm additional padding and up to about 10 cm. The sample storage device holder also contains space for a secure fit of an information device. The location of the information device holder within the transportation sleeve depends on the type of information device. It is designed to provide a snug fit for either one or multiple CDs or memory cards/memory sticks. The sample storage device holder is produced preferably of formable material, such as cardboard or foam based. The sample storage device holder including the padding material is either surrounded by an outside enclosure or is integrated into an enclosure surrounding the sample storage device(s) and the information storage device from all six sides including an opening lid or surrounding the sample storage device holder from 5 sides. In case the sample storage device holder includes an opening lid, the lid is attached to one of the sides of the sample storage device holder, covers one of the sample storage device holder sides and attaches to the opposite side and securely closes the transport sleeve. For the 5-sided sample storage device holder surrounding the closure of the 6th side is provided through a closing box, sliding over the entire sample storage device holder. The enclosure can be of package material providing rigidity to the sample storage device holder. Space is provided on the outside of the transport sleeve for address labels and postage stamps.

Protein Crystallography Module

The crystallography module contains wells that may be filled with different protein crystallization solutions and dehydrated. The basic storage device may be produced out of clear see-through plastic and each individual well contains a protein crystallization condition spanning the pH range from about 4.6 to about 9.4, Each well may contain different buffers such as but not limited to acetate, tartrate, phosphate, Tris, citrate, HEPES, imidazole, formate, cacodylate, MES, Bicine, Tris, citrate, HEPES, acetate and different precipitating salts such as tartrate, phosphate, ammonium and lithium sulfate, magnesium and calcium chloride, magnesium, ammonium, sodium, zinc and calcium acetate, sodium citrate, sodium and magnesium formate, magnesium and sodium chloride, sodium acetate, sodium citrate, ammonium formate, lithium and ammonium sulfate, imidazole, CTAB and precipitating organic solvents like MPD, 2-propanol, ethylene glycol, dioxane, ethanol, 1,6-hexanediol. They can also contain PEG 400, 6000, 1000, 8000, 10000, and 20000, PEG MME 550, 2000, 5000, and 2000, Jeffamine M-600 or other additives like tert-butanol, glycerol, $Co^{2+}$, $Cd^{2+}$, $Fe^{3+}$, $Ni^{2+}$, and $Zn^{2+}$ ions, dioxane, ethylene glycol, polyethyleneimine. The wells may be filled with the solutions above at different concentrations. The wells are dehydrated, retaining the substances on the walls of the wells. The wells are ready to use, can be rehydrated with water and the protein may be added.

Stacking Rack

The individual sample storage units may be stored either at room temperature or refrigerated in specially designed storage rack. The rack (see Figures) may hold different amounts of sample storage units, the barcode is preferably visible and the units may slide easily on plastic tracks. The storage rack may be either open or enclosed in a plastic box with closing door.

The stacking rack can be produced out of plastic or metal. It may hold 10, 25 or 50 sample storage devices. The sample storage devices slide on tracks into the stacking rack. A locking mechanism prevents the cards from falling out of the stacking rack. The stacking rack can be either open or may be completely enclosed by protective material and one hinged door at the front side of the stacking rack.

System for Storing, Tracking, and Retrieving Data Associated with Biological Materials The foregoing storage device in the various embodiments described above can be combined with other technologies to provide for integration of sample storage and sample management for life science applications. This embodiment of the invention enables the integration of biological sample storage, location, tracking, processing, and sample data management. Data regarding samples can be associated with the location of the samples through direct physical association of the data with the sample storage devices. The stored information can be updated with additional data that originates from inventory and tracking of samples in combination with multi-step biological research protocols, production processes, screening, bioassays, patient histories, clinical trial data, and other sources of developed information. The data associated with the sample can be transmitted and shared through a secure hierarchical software and networking architecture that enables interfacing of multi-user, multi-site environments.

Ideally, information about a sample is integrated with the sample storage device by an associated electronic interface, preferably a wireless interface, such as a radio frequency identification (RFID) transponder. While barcodes have been used in the past to identify samples, this technology has limitations that make it unsuitable for use in the present invention. These limitations include the required line-of-sight access to the barcode for transfer of information, limited information capacity, and interference through environmental factors such as dust, moisture, and the like. Radio frequency identification technology overcomes these disadvantages.

Remote communication utilizing wireless equipment typically relies on radio frequency (RF) technology, which is employed in many industries. One application of RF technology is in locating, identifying, and tracking objects, such as animals, inventory, and vehicles. Examples of publications disclosing RF identification tag systems include the disclosures of U.S. Pat. Nos. 6,696,028; 6,380,858; and 5,315,505.

Figure 9:
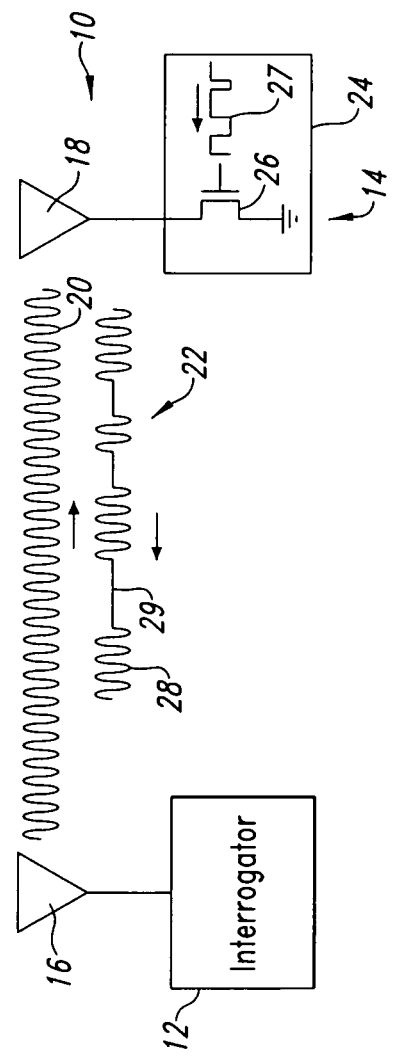
FIG. 9 is a schematic diagram of a known radio-frequency communication system.

RF identification (RFID) tag systems have been developed that facilitate monitoring of remote objects. As shown in FIG. 9, a basic RFID system 10 includes two components: an interrogator or reader 12, and a transponder (commonly called an RF tag) 14. The interrogator 12 and RF tag 14 include respective antennas 16, 18. In operation, the interrogator 12 transmits through its antenna 16 a radio frequency interrogation signal 20 to the antenna 18 of the RF tag 14. In response to receiving the interrogation signal 20, the RF tag 14 produces an amplitude-modulated response signal 22 that is transmitted back to the interrogator 12 through the tag antenna 18 by a process known as backscatter.

The conventional RF tag 14 includes an amplitude modulator 24 with a switch 26, such as a MOS transistor, connected between the tag antenna 18 and ground. When the RF tag 14 is activated by the interrogation signal 20, a driver (not shown) creates a modulating on/off signal 27 based on an information code, typically an identification code, stored in a non-volatile memory (not shown) of the RF tag 14. The modulating signal 27 is applied to a control terminal of the switch 26, which causes the switch 26 to alternately open and close. When the switch 26 is open, the tag antenna 18 reflects a portion of the interrogation signal 20 back to the interrogator 12 as a portion 28 of the response signal 22. When the switch 26 is closed, the interrogation signal 20 travels through the switch 26 to ground, without being reflected, thereby creating a null portion 29 of the response signal 22. In other words, the interrogation signal 20 is amplitude-modulated to produce the response signal 22 by alternately reflecting and absorbing the interrogation signal 20 according to the modulating signal 27, which is characteristic of the stored information code. The RF tag 14 could also be modified so that the interrogation signal is reflected when the switch 26 is closed and absorbed when the switch 26 is open. Upon receiving the response signal 22, the interrogator 12 demodulates the response signal 22 to decode the information code represented by the response signal. The conventional RFID systems thus operate on a single frequency oscillator in which the RF tag 14 modulates a RF carrier frequency to provide an indication to the interrogator 12 that the RF tag 14 is present.

The substantial advantage of RFID systems is the non-contact, non-line-of-sight capability of the technology. The interrogator 12 emits the interrogation signal 20 with a range from one inch to one hundred feet or more, depending upon its power output and the radio frequency used. Tags can be read through a variety of substances such as odor, fog, ice, paint, dirt, and other visually and environmentally challenging conditions where bar codes or other optically-read technologies would be useless. RF tags can also be read at remarkable speeds, in most cases responding in less than one hundred milliseconds.

A typical RF tag system 10 often contains a number of RF tags 14 and the interrogator 12. RF tags are divided into three main categories. These categories are beam-powered passive tags, battery-powered semi-passive tags, and active tags. Each operates in fundamentally different ways.

The beam-powered RF tag is often referred to as a passive device because it derives the energy needed for its operation from the interrogation signal beamed at it. The tag rectifies the field and changes the reflective characteristics of the tag itself, creating a change in reflectivity that is seen at the interrogator. A battery-powered semi-passive RF tag operates in a similar fashion, modulating its RF cross-section in order to reflect a delta to the interrogator to develop a communication link. Here, the battery is the source of the tag's operational power. Finally, in the active RF tag, a transmitter is used to create its own radio frequency energy powered by the battery.

Figure 10:
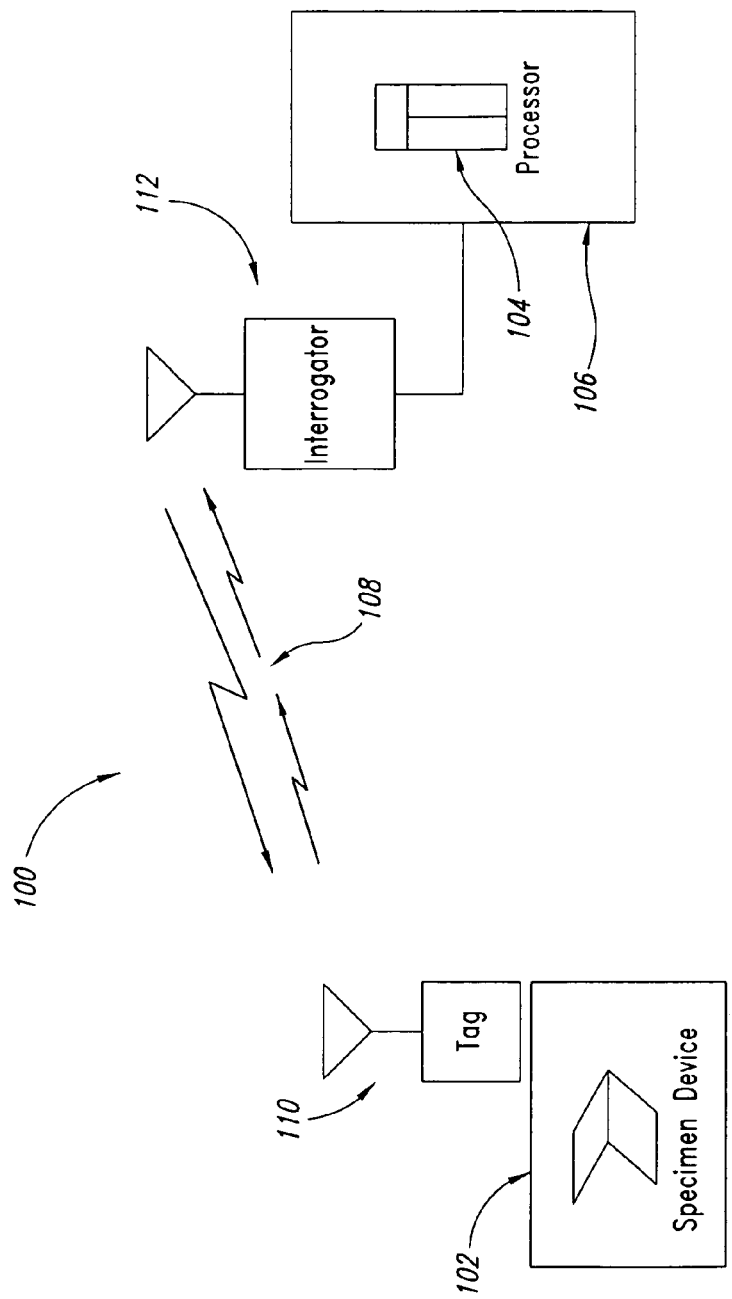
FIG. 10 is a schematic diagram of a system formed in accordance with one embodiment of the present invention.

In a preferred embodiment of the present invention, the system consists of three parts, a consumable hardware device, inventory and management software, and the RFID interface between the hardware device and the software. Referring to FIG. 10, shown therein is a system 100 formed in accordance with one embodiment of the invention to include the storage device 102 described above, the inventory and management software component 104, preferably implemented in a computer system 106, and the radio frequency identification interface 108 coupling the storage device 102 and the software 106. Preferably, the RFID interface 108 includes a transponder 100 associated with the storage device 102 and an interrogator 112, which is coupled to the computer-implemented system 106.

In this embodiment, the transponder 110 is associated with the sample storage device 102, such as by affixing the transponder 110 to an exterior surface of the storage device 102. However, it is to be understood that the transponder 110 can be affixed to or associated with a tube, a plate, a rack, or even a room in which the storage device 102 is maintained. While it is preferred that a single transponder 110 be associated with a single storage device 102, it is possible that each particular sample stored in the storage device 102 can have a transponder 110 associated with it.

Association can be achieved either during production of the storage device 102 such that the transponder 110 is embedded in the storage device 102 or after the storage device 102 has been produced, such as through adhesive affixation to the storage device 102. Inasmuch as magnetism is the preferred connecting mechanism used in the sample storage device 102 in its various embodiments, it will be understood by one of ordinary skill in this technology that appropriate shielding may be needed to prevent unintentional altering of information stored in the transponder 110 and to prevent interference with radio frequency communications between the transponder 110 and the interrogator 112.

The transponder 110 can be preprogrammed with data about the storage device 102 and the samples stored in the storage device 102, including ownership information, location information, analysis information, production processes, clinical trial conduct, synthesis processes, sample collections, and other information known to those skilled in the art that would be of value in managing samples. In addition to preprogramming such data, the transponder 110 can be configured to permit modification and updating of the data within its memory. In addition, the transponder 110 will contain security architecture that defines precise access conditions per type of data to thereby restrict reading, writing, and updating. For example, the RFID interface 108 components can be configured to receive control signals from and to respond to a particular computer-implemented data processing system, such as the software application described herein below. In addition, data written to the transponder 110 can be encrypted for authentication and security purposes.

The use of RFID transponders or chips offers the benefit of a wide temperature range (−25° C. to +85° C.) without the loss of functionality. In addition, the transponders 110 can be utilized to control remote devices, such as a signaling light or generator of audible tones for alerting and locating the object associated with the transponder 110. Storage of information in the transponder 110 also provides an additional backup should data in the computer-implemented system 106 be damaged or lost.

The interrogator 112 is a conventional radio frequency identification reader that is coupled to the computer-implemented system 106. Command and control signals are generated by the system 106 to initiate interrogation of one or more transponders 110 and to receive a response therefrom that is processed by the software 104 in the computer-implemented system 106. In one configuration, the transponders 110 can be reprogrammed via communications from the interrogator 112 to replace or update data stored therein.

In one implementation, one or more interrogators 112 are positioned within a facility at a sufficient range to communicate via radio frequency signals, such as microwave signals, with the transponders 110. Multiple interrogators 112 can be used for multiple classes of transponders 110 or with individual transponders 110. Alternatively, one interrogator utilizing known technology can communicate with multiple transponders 110 on multiple frequencies in serial fashion or concurrently. In applications where a sample storage device 102 or individual samples are processed, multiple interrogators positioned at various locations within a structure or along a path of travel, such as a conveyor system or a shipping system, such as freight lines, trains, and the like, can be used to track the location and the status of the sample. This includes checking environmental factors, such as temperature, humidity, pressure, and the like in which the specimen or storage device 102 is located.

Thus, the RFID interface 108 can be expanded to monitor and process data related to the movement and analysis of a sample or storage device 102 located in a laboratory, manipulated by laboratory robots, and the like such as during biological production processes or the execution of experimental steps. This also aids in quality control and in processing biological samples through automated or semi-automated research protocols.

As mentioned above, sample storage and tracking are facilitated by locating a sample through the use of an RF interface between the RF transponder on the sample storage device and the computer-implemented system described herein, which is achieved through the tagging and monitoring of the storage location, such as a storage rack, a storage room, a refrigerator, a lab bench, a desk, or a bookshelf.

In order to trace a particular storage device 102 or sample, the transponder 110 is configured to activate a remote device, such as a blinking light located on the storage device, an audible device associated with the storage device, or a color change of the storage device that can be recognized by a person or by an automated system, to enable fast retrieval of the sample. In addition, the transponder 110 is configured to activate a remote alarm when an environmental condition has exceeded a predetermined environmental range, including but not limited to temperature, pressure, and humidity. In one embodiment, the transponder 110 is a passive device that is activated by the interrogation signal, from which it draws operating power. When the transponder 110 is used to activate a remote device or to increase the range of communication, the transponder can be semi-active as described above. Alternatively, an active transponder can be used when large amounts of data are to be read from or written to the transponder 110 or increased range as desired. Range is also affected by frequency, as is known in the art, and one of ordinary skill would select the appropriate frequency range in accordance with the environment, and the functional objectives. For example, certain specimens may be sensitive to particular frequencies of radio signals, and such frequencies would need to be avoided or the specimen appropriately shielded when designing the system 100.

The inventory and management software 104 is tailored for use with wireless communication systems and the processing of data associated with the life sciences. It consists of a customized user interface and a set of predefined database tables in one embodiment. A user can enter sample-associated data or import information from outside sources. Predefined tables are provided in the database to facilitate setup of the system, but a user can have the option to customize fields within the tables. The relational database can include tables for DNA sample, clones, oligonucleotides, PCR fragments, cDNA chemical compounds, proteins, metabolites, lipids, cellular fractions, biological samples from different organisms such as viruses, bacteria, or multi-cellular organisms, patient samples such as blood, urine, and buccal swabs. Detailed sample information and sample-associated data is programmed into the tables. Sample information can for example include sample source, clone name, gene insert name, insert size, insert sequence, modifications, vector name, vector size, antibiotic selection, induction, terminator, cloning sight, 5'-tag, 3'-tag, purification tag, oligonucleotide name, purification, quality control, forward primer, reverse primer, $T_m$ value, and size selection. Clinical patient information can be, for example, age, gender, location, ethnic group, body mass index, family history, medication, data of onset of symptoms, duration of disease, and medical tests. Sample-associated data can consist of research data from various sources, such as, for example, sequence information from a DNA sequencer, transcriptional profiling information from microarray chips, protein data from Western blotting or in-situ hybridization, bioassay data for drug discovery, high through-put drug screening data, chemical library synthesis data, and the like. Data can be supplied in the form of text, numbers, tables, or images.

The software can also link to other data sources and integrate information from public domains, such as GenBank, SwissProt, and other similar domains or proprietary sources. Ideally the software is able to interface with robotics equipment to track the sample within a process, and tracking of the process can be displayed as an accumulative sample history for storage within the sample device as well as the database, such as storage in an RFID transponder 110.

The software is designed to create an informatics infrastructure where a single user generates their data and information set, which is initially stored at a local workstation in a local database format. However, the software is capable of linking multiple users in a hierarchical environment. The information accumulated by a single user can best be up-loaded to a centralized database system on a server. The interaction of the network environment can also be a web browser interface. The multi-user environment can be expanded to multiple-site environments, and software and databases can be located on a personal computer, on a server within an intranet or on the internet such as an e-commerce site. Access control and log control systems are also provided in the software.

Figure 11:
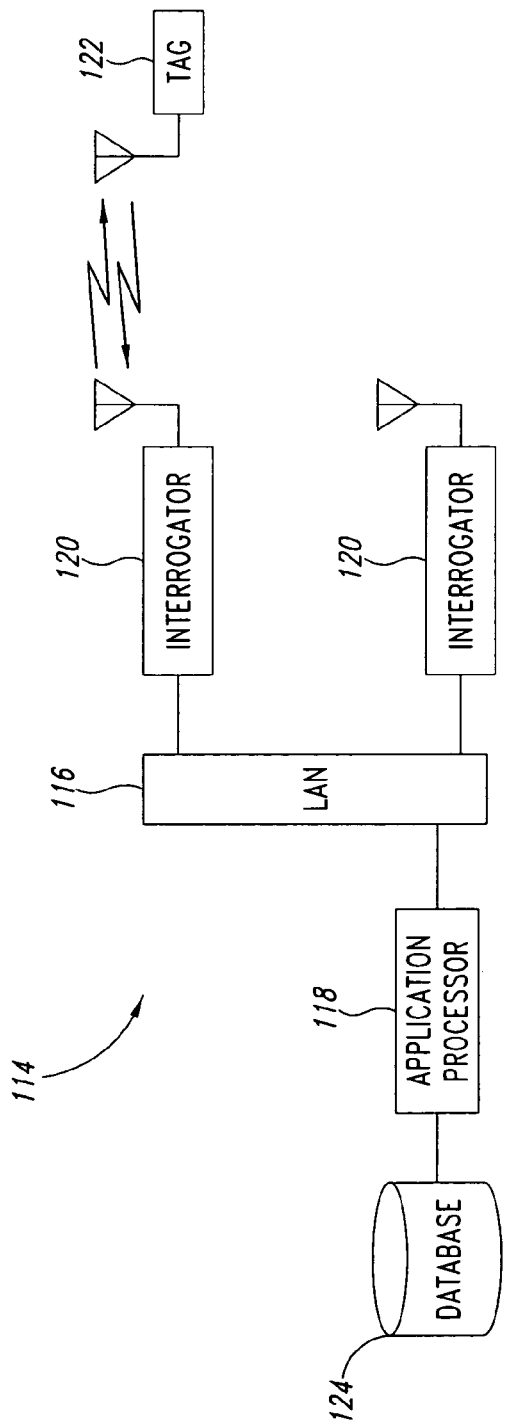
FIG. 11 is a block diagram of a computer-implemented system architecture formed in accordance with another aspect of the present invention.

Shown in FIG. 11 is a computer-implemented system architecture 114 for utilizing a local area network 116 to interface an application processor 118 with one or more interrogators 120 that communicate with one or more remote RFID tags 122. The application processor 118 is coupled to a database 124 It is to be understood that the local area network can instead be a global network, such as the Internet, in which case web-based applications would be utilized.

Ideally, in one embodiment the inventory and management software 104 has three components, a front end software component, a middleware component, and a back end software component.

It is envisioned that the front end software is utilized to create a "user interface." This can be, for example, a web browser or Microsoft Excel. The web browser software Would be used for a web-based system 100, whereas the Microsoft Excel software would be used for a desktop system. The web-based option provides for multiple users, networking, and can be expanded to accommodate thousands of users. The desktop option is sufficient for a single user who does not anticipate sharing of data and sample information via a network.

The middleware can include Microsoft Excel macros developed for use as a desktop option or custom software created by programming language suitable for use with web-based systems, such as PHP. The middleware is configured as a collection of programs that is capable of receiving user inputs and queries and returning database information to the user via known output, such as printer, display, or audible output.

The back end software is preferably Microsoft Access, which is proprietary database software offered by Microsoft Corporation and hosted by Microsoft Excel. This particular program provides sufficient database capacity to support up to 50,000 records, and to a maximum of 100,000 records with increasing levels of performance degradation. Another option is MySQL, which is a freeware database software developed collaboratively and available at no charge that runs on all major servers, including those based on Windows and Linux platforms. This database is capable of handling millions of records, and would be suitable for the large institutional user, such as governmental agencies, universities, and multinational entities.

The software 104 is configured to provide control signals to the RFID interface 108 and to receive data and information from the interface 108. In addition, when information is supplied to a transponder, the software 104 is configured to initiate writing of the data through the interrogator 112 to the transponder 110 using methods and equipment known in the art and which is readily commercially available.

Figure 12:
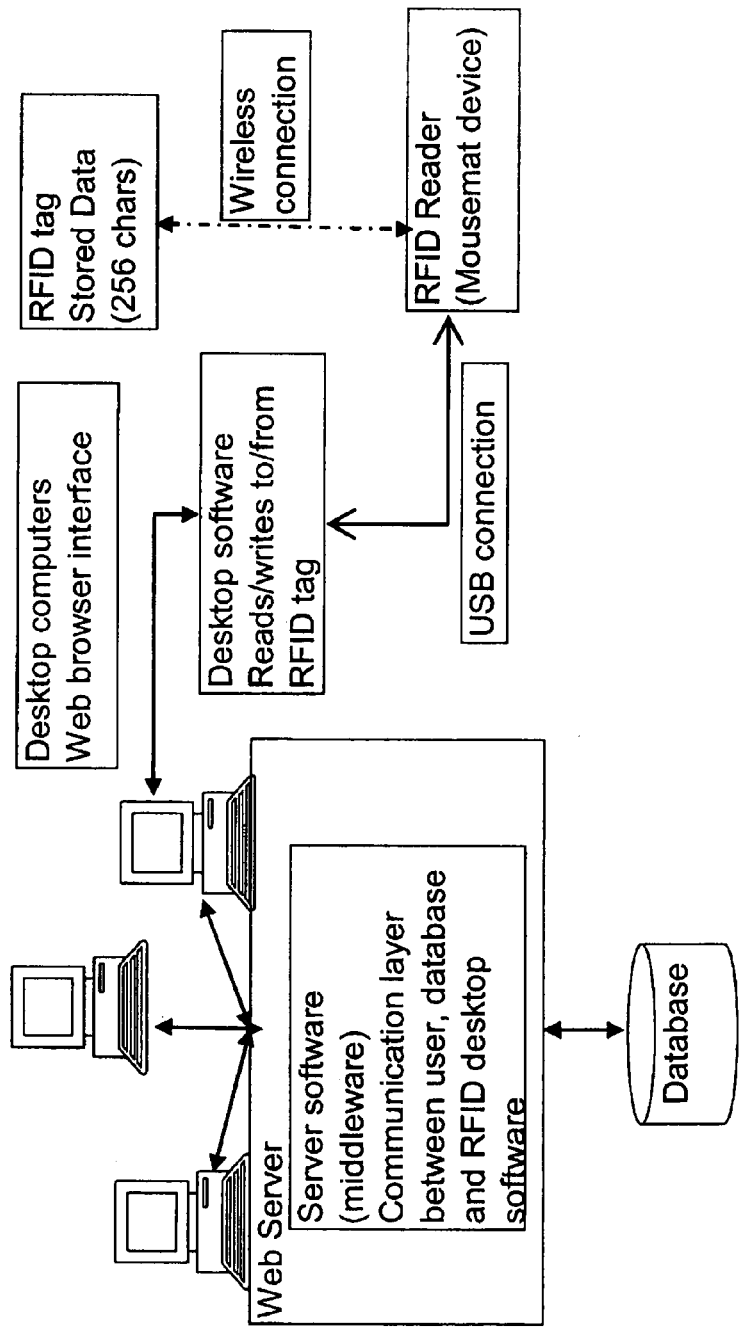
FIG. 12 shows a computer-implemented system architecture in accordance with certain invention embodiments.

FIG. 12 illustrates another system architecture 128 in which a database 130 is linked to a plurality of desktop computers 132 via a web server 134. Resident on the server 134 is software that provides a communication layer between the user, the database 130, and desktop software 136 resident on the desktop computers 132. With a web browser interface 138, a user can connect to the RFID reader 142 through a standard USB connection 140. The user can then control read and write operations of the RFID reader 142 and the remote RFID tag 144 using the wireless connection 146 provided by the radio frequency communications.

Figure 13:
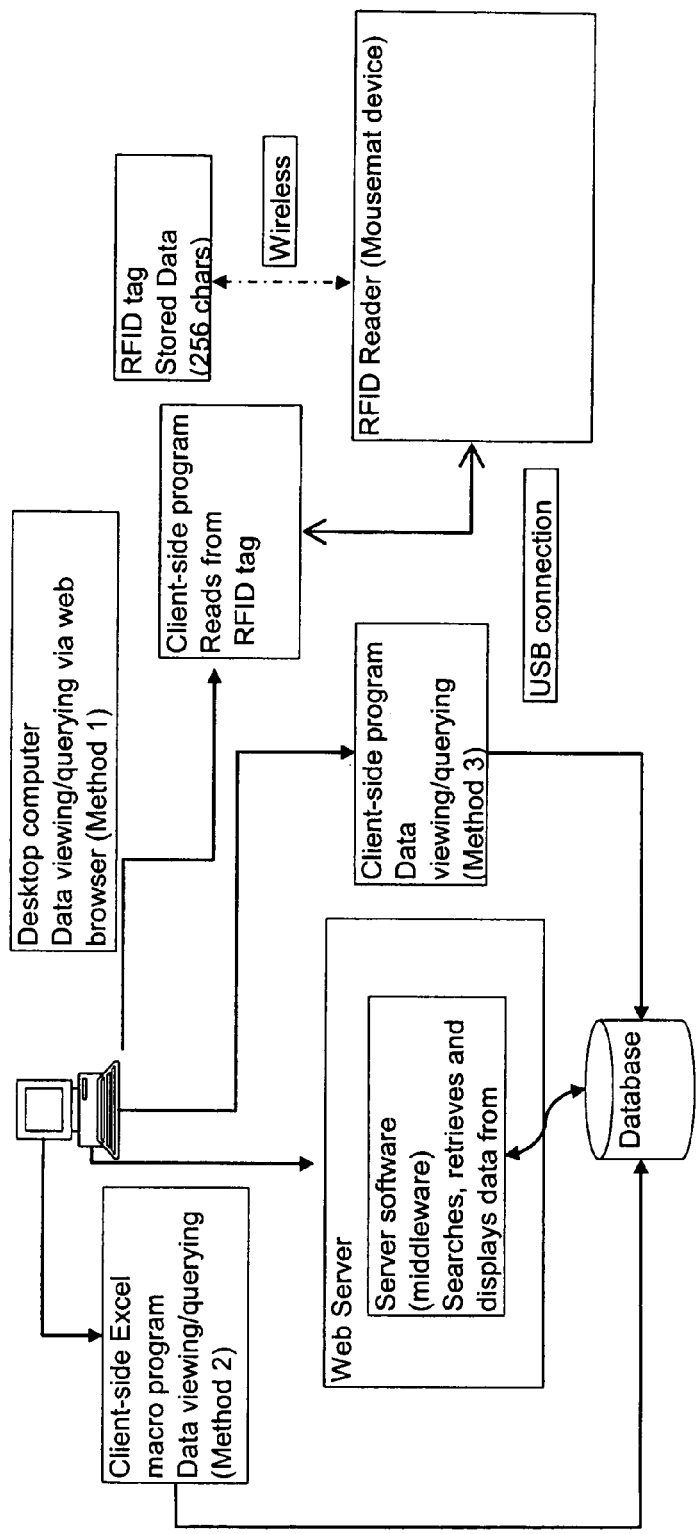
FIG. 13 shows a computer-implemented system architecture in accordance with certain invention embodiments.

Referring next to FIG. 13, shown therein is a further embodiment of the invention utilizing a 3-tier architecture 148 having a desktop computer 150 with a front-end web browser 158 linked to a backend database 154 via web server middleware 156 on a web server 152. The middleware search, retrieval, and display ability to a user. More particularly, the business logic is contained in the middleware program 156 on the web server 152. In addition, there is (optionally) an RFID reader 160 coupled via a USB connection 162 to the client-side program 164 on the desktop computer 150. The client-side application, which reads and writes to the RFID tag 166 via the reader 160, is launched from the web browser 158.

In an alternative 2-tier arrangement of this architecture 148, there is an Excel front-end program on the desktop computer 150 that communicates directly with the database 154 at the back end. The business logic here is embodied in the Excel macro program. This method is particularly efficient for loading data (e.g., 96 rows of data corresponding to each well in a plate) into a database to take advantage of the Excel functions, such as copying, dragging down, etc.

In a further alternative 2-tier arrangement of the architecture 148, a stand-alone client application 170 at the front end communicates directly with the database 154 at the back end. The business logic is contained within the stand-alone client application, and a module for reading from and writing to the RFID tag 166 may also be contained within this application 170. Here the advantage is that the application is compiled (the source code is not visible) and does not require third-party software (Excel, web-server). The drawback is that it is not as network compatible as the 3-tier architecture described above.

The following Examples are presented by way of illustration and not limitation.

EXAMPLES

Example 1

Preparation of Matrix for Biological Sample Storage Device

This example describes preparation of biological sample storage devices using a dissolvable matrix material. Dependent on the biological material being stored in a particular example, the matrix was prepared with different storage buffers. In these Examples, all reagents were from Sigma (St. Louis, Mo.) unless otherwise noted. For dry storage of nucleic acids, 20 mM Tris pH 6.5 was used for the preparation of a 1% polyvinyl alcohol (PVA, Sigma no. P8136) basic storage matrix. The concentration of the polymer was tested in a range of 0.1% to 10% (v/w). The pH of the matrix was tested in the range of pH 5 to 8. For convenient detection of biological sample phenol red was added to the liquid matrix at 0.0002% (w/v).

The matrix in liquid form was applied to sample wells of a 96-well plate and dried completely at room temperature either under standard pressure or under vacuum in a vacuum chamber. The drying time for a 50 µl volume of matrix was overnight and under vacuum a shorter drying time was required. The plates were then ready for the storage of biological material.

Additional storage additives such as one or more of EDTA, NaCl, $MgCl_2$, KCl, $(NH_4)_2SO_4$, $MgSO_4$, $CaCl_2$, Zn-acetate, Na-Acetate, cysteine, dithiothreitol (DTT, Cleland's reagent), potassium acetate, Tris-acetate, magnesium acetate, $KPO_4$, glycerol, Triton X-100®, sodium dodecyl sulfate (SDS), sodium azide, protease inhibitors (PMSF, aminoethylbenzenesulfonyl fluoride, pepstatin, E64, bestatin, leupeptin, aprotinin), 2-mercaptoethanol, polyethylene glycol (PEG), bovine serum albumin (BSA), nicotinic adenine dinucleotide (NAD), ATP may be added directly into the storage matrix for stabilization and activation after rehydration, depending on the bioactivity to be tested. For biological material associated with biological activity such as enzymes, the reaction conditions may be adjusted directly in the storage matrix. In some cases the only substance to be added for rehydration prior to an activity reaction is water. The matrix can also include one or more inhibitors such as antibacterial and/or antifungal agents. The matrix can be sterilized through sterile filtration or autoclaving prior to aliquoting the matrix into the individual storage wells. The autoclaved matrix is applied in aliquots to the storage wells either in single tubes or in multiwell plates at a liquid volume of 10 to 100 µl per well in the case of a 96-well plate.

Example 2

Dry Storage of Nucleic Acids

Biological sample storage devices were prepared as described in Example 1. General molecular biology materials and methods were used, as described. (Sambrook et al., *Molecular Cloning: A Laboratory Manual*, Cold Spring Harbor Laboratories, Cold Spring Harbor, N.Y., 2001; Ausubel et al., 1993 *Current Protocols in Molecular Biology*, Greene Publ. Assoc. Inc. & John Wiley & Sons, Inc., Boston, Mass.). Stability tests were performed for plasmids, oligonucleotides, DNA fragments in the form of a 1 kB ladder, PCR products, genomic DNA (feline and human) and RNA. Recovery and stability tests were performed using gel based, PCR, and transformation rate analyses.

A. Plasmid Storage

A total of 50 ng of circular plasmid (puc19) (New England Biolabs Inc., Beverly, Mass.) at a concentration of 10 ng/µl in double distilled water ($ddH_2O$) was spotted on the dried dissolvable matrix in each well of a 96-well polypropylene plate. The sample was dried and stored at room temperature. Control plasmid was stored in liquid form in a −20° C. freezer. For recovery, 50 µl of $ddH_2O$ was applied to the dry sample well. The sample was re-hydrated for 15 minutes and 10 µl aliquots were used to transform DH5-alpha competent bacterial cells. The transformed cells were plated on LB agar plates and incubated overnight at 37° C. The cells on each plate were counted. Percent DNA recovery was calculated based on the transformation of control DNA (10 ng of puc19 stored at −20° C.).

DNA recovery was greater than 500% on a 5% PVA matrix following storage for over 8 months. A 1% PVA matrix was tested at the 1 month time point and resulted in recovery that was greater than or equivalent to the freezer-stored DNA. Transfection rate for long-term storage was stable with a recovery of 60% for 5% PVA matrix and 100% for the 1% matrix. No decrease in recovery was observed after 6 months of storage. 5% PVA did not go into solution completely.

PCR analysis of the rehydrated sample demonstrated continued stability of the sample under the conditions described. Two PCR primers were designed (forward and reverse) amplifying a 480 bp stretch of the puc19 plasmid. 5 ng of rehydrated sample was used for the amplification reaction in comparison to 5 ng of control plasmid. The PCR reactions were performed at low cycle numbers under nonsaturating conditions. After 8 months the dry stored material could be amplified without detectable loss of amplification efficiency.

B. Oligonucleotide Storage

Two olgionucleotides (PCR primer forward and reverse) for the amplification of puc19 were spotted in a volume of 10 µl at a total concentration of 10 µM and 20 µM each on a 1% PVA dry storage matrix in each well of a 96 well plate. The oligonucleotides were dried overnight at room temperature and the plate was stored at room temperature. Control oligonucleotides were stored in liquid form in a −20° C. freezer. For recovery, wells containing both oligonucleotides (PCR primers) were rehydrated using PCR reagents containing 1×PCR buffer, 5 ng of puc19 plasmid and dNTPs for 15 minutes. The rehydrated reaction mixture was transferred into PCR tubes and Taq polymerase was added. The reaction was cycled for 25 cycles and electrophoretically analyzed on a 1% agarose gel.

The gel analysis revealed the amplification of a PCR product of expected size. Compared to the control, twice the amount of primer was required to obtain the same amount of amplification compared to liquid stored primer. Recovery rate from a 1% PVA matrix was lower than the liquid stored control. Recovery was improved by reducing the concentration of PVA in the matrix.

C. DNA Fragment Storage

DNA fragments in the form of a 1 kb DNA ladder (Invitrogen) (0.5 ug) size standard were spotted onto a 1% PVA based dry storage matrix in the presence of DNA loading buffer containing phenol red or other coloring agent and 50% glycerol. Each well was spotted with 10 ul of DNA ladder and dye, equivalent to the volume of fresh DNA ladder used for the visualization of the ladder in one well of an electrophoresis agarose gel. The DNA fragments with the loading dye were dehydrated overnight and stored at room temperature. For recovery, cells with the 1 kB DNA ladder size standard and loading buffer were rehydrated with 10 µl of $ddH_2O$. The rehydration time was 5 and 10 minutes respectively, prior to loading of the 10 µl of 1 kB ladder onto an electrophoresis gel.

For analysis, 10 µl of control ladder stored in liquid form in the presence of loading buffer at −20° C. was compared by fluorescence intensity using Ethidium Bromide stain to the 5 minute and 10 minute rehydrated dry stored size standard. No difference in fluorescence intensity of the different size DNA bands was observed. None of the bands showed DNA degradation from the dry storage at room temperature.

D. Genomic DNA Storage a) Genomic Feline DNA

A total amount of 20 ng total genomic feline DNA in 10 µl of TE pH8 buffer was spotted onto a $^5$% PVA based dry storage matrix per well of a 96 well plate. The genomic DNA was dried overnight and stored at room temperature. Control DNA was stored frozen at −20° C. For recovery, the wells containing the genomic feline DNA were rehydrated using PCR reagents containing 1×PCR buffer, 2 feline specific primers at a concentration of 10 µM and dNTPs for 15 minutes. The primers amplified a 600 bp fragment of feline DNA. The rehydrated reaction mixture was transferred into PCR tubes and Taq polymerase was added. The reaction was cycled for 35 cycles and analyzed on a 1% agarose gel.

PCR analysis was performed one week and 3.5 months after dry storage. At both time points the DNA fragment of expected size could be amplified without a decrease in amplification rate compared to frozen stored genomic DNA.

b) Genomic Human DNA

A total amount of 20 ng total genomic human DNA in 10 µl of TE pH8 buffer was spotted onto a 1% PVA based dry storage matrix in each well of a 96 well plate. The genomic DNA was dried overnight and stored at room temperature. Control DNA was stored frozen at −20° C.

Wells containing the genomic human DNA were rehydrated during PCR reagents containing 1×PCR buffer, 2 human growth factor 13 (hFGF13) specific primers at a concentration of 10 µM and dNTPs for 15 minutes. The rehydrated reaction mixture was transferred into PCR tubes and Taq polymerase was added. The reaction was cycled for 35 cycles and analyzed on a 1% agarose gel.

PCR analysis was performed one month after dry storage. The fragment of the human growth factor gene of expected size was amplified without a decrease in amplification rate compared to frozen stored genomic DNA.

Example 3

Dry Storage of Proteins

Biological sample storage devices were prepared as described in Example 1. This example shows that dry storage of proteins at ambient temperature with complete recovery of activity offer tremendous advantages compared to storage of proteins frozen as liquid samples.

Stability and activity tests for different sequenases, heat stable polymerases, restriction enzymes, ligases, proteases were performed to demonstrate the protective nature of the dissolvable matrix. Stabilization of proteins and their recovery as active molecules was achieved using the longterm dissolvable matrix described above. The matrix was prepared in the presence of TRIS pH5-8; phenol red as a pH indicator, and 1% PVA. The matrix was solidified by dehydration and the proteins were spotted onto the dried matrix in the presence or absence of trehalose (Fluka, cat. no. 90210) or validamycin A (Research Products International Corp., catalog no. V21020) in liquid form. The water in the protein solution hydrated and solubilized the PVA. The protein mixture soaked into the solubilized matrix and dried at ambient temperature. Validamycin A was added to the biological material in a concentration of 0.5 to $^{10}$% w/v. The mixture of biological sample in the presence of validamycin A was applied to the dissolvable PVA sample matrix.

Example 4

Longterm Storage of Proteins Using the Dissolvable PVA Matrix

This example describes recovery of active proteins following longterm dry storage on dissolvable PVA matrices prepared as described in the preceding examples.

A. Polymerases

1) SEQUENASE™—Sequenase™ (USB, Cleveland, Ohio) is normally stored at −20° C. and loses activity over time in the freezer through repeated freeze thaw, resulting in reduced reading length and quality of the sequencing reaction. Sequenase™ was applied to the dissolvable matrix in 1×sequencing buffer in the presence of 5% final concentration of trehalose or validamycin A. USB Sequenase™ Version 2.0, DNA sequencing kit (product number 70770) was used according to suppliers protocol. The concentration per well in a 96 well plate was equivalent to the concentration of frozen stored Sequenase™ used for one sequencing reaction. Control Sequenase™ was stored conventionally, in a −20° C. freezer. For recovery, the complete well was hydrated with 20 µl of 1×sequencing buffer for 5-45 minutes.

For activity analysis, sequencing reactions were prepared using an $S^{35}$ label and the reaction was electrophoresed on an acrylamide sequencing gel. The sequences of the frozen and the dry stored sequenase were compared by reading the sequence ladders. Both sequences had the same reading quality.

2) TAQ POLYMERASE—Taq polymerase for PCR reactions is stored at −20° C. and loses activity over time through repeated freeze thaw resulting in lower amplification efficiency. The Taq polymerase (5 U per well) was applied to the dissolvable matrix in 1×PCR buffer in the presence of 5% final concentration of Trehalose or Validamycin A. The concentration per well in a 96 well plate was equivalent to the concentration of frozen stored Taq polymerase used for one PCR reaction. Control Taq polymerase was stored conventionally in a −20° C. freezer. For recovery, the complete well was hydrated with 20 ul of 1×PCR buffer for 5-45 minutes.

For activity analysis, PCR reactions were prepared using standard PCR protocols and the PCR product was electrophoresed on an agarose gel. The PCR products of the frozen and the dry stored polymerase were compared by visual inspection. Both PCR products were equal in intensity.

Figure 14:
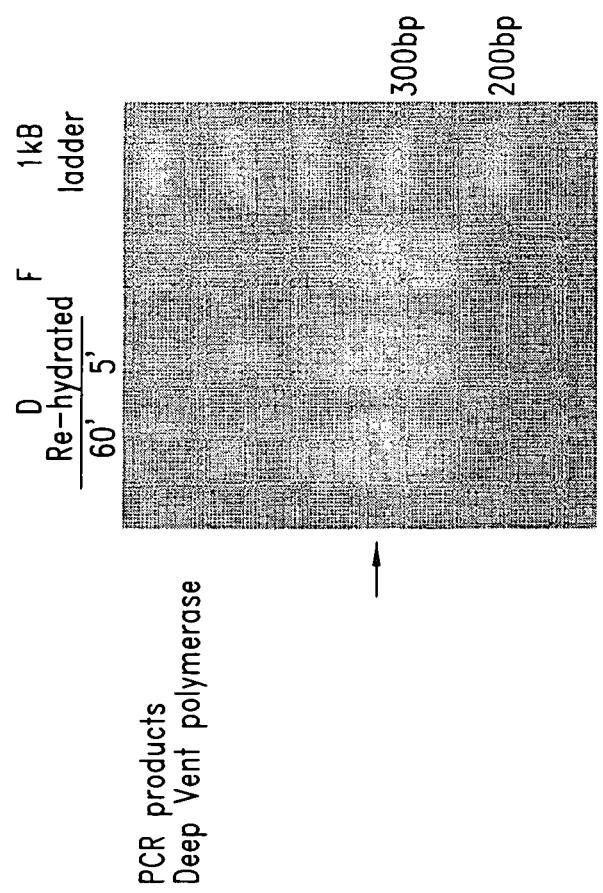
FIG. 14 shows a gel with PCR products of Deep Vent™ Polymerase. Deep Vent™ polymerase was stored at ambient temperature (D) and was hydrated for either 60 minutes (D 60') or 5 minutes (D 5') in the presence of reaction buffer, template, dNTPs and primers. A frozen stored Deep Vent polymerase (F) was used as a control. The arrow indicates the PCR product of expected size.

3) DEEP VENT™ HIGH FIDELITY POLYMERASE (New England Biolabs Inc, Beverly, Mass.) Deep Vent™ polymerase for PCR reactions was shipped on dry ice and stored at −20° C. If the frozen chain of transport was interrupted the enzyme lost its activity. The protein lost activity over time through repeated freeze thaw, resulting in reduced enzyme activity. Fully active Deep Vent™ polymerase was applied to the dissolvable PVA matrix in 1×PCR buffer in the presence of 5% final concentration of Validamycin A. The concentration per well in a 96 well plate was (5 U per well), equivalent to the concentration of frozen stored Deep Vent™ Polymerase used for one PCR reaction. Control Deep Vent™ Polymerase was stored in a −20° C. freezer. The complete well was hydrated with 20 pl of 1×PCR buffer for 5-45 minutes. PCR reactions were prepared using standard PCR protocols and the PCR product was electrophoresed on an agarose gel. As shown in FIG. 14, the PCR products of the frozen and the dry stored sequenase were compared by visual inspection. Both PCR products were equal in ethidium bromide intensity. No quantitative difference could be detected between a re-hydration time of 5 minutes versus 60 minutes.

B. Restriction Enzymes

HindIII was spotted at 20 U and 40 U per well was applied to the dissolvable matrix in 1×digestion buffer in the presence of 5% final concentration of Trehalose or Validamycin A. The concentration per well in a 96 well plate was equivalent to the concentration of frozen stored Taq polymerase used for one PCR reaction. Control HindIII was stored conventionally in a −20° C. freezer. The complete well was hydrated with 20 pl of 1×restriction enzyme buffer for 5-45 minutes. 1 ug of puc19 plasmid was digested with the rehydrated restriction enzyme and the digested plasmid was electrophoresed on an agarose gel. The DNA banding pattern of the frozen and the dry stored HindIII were compared to a nondigested plasmid by visual inspection. The frozen and the dry stored enzyme showed equivalent activity.

C. BIG DYE™ CYCLE SEQUENCING—ABI Big Dye™ (Applied Biosystems Inc., Foster City, Calif.) enzyme for cycle sequencing lost activity over time after repeated freeze thaw processes, resulting in reduced reading length of the sequencing reaction and reduced quality of the read.

Figure 15A:
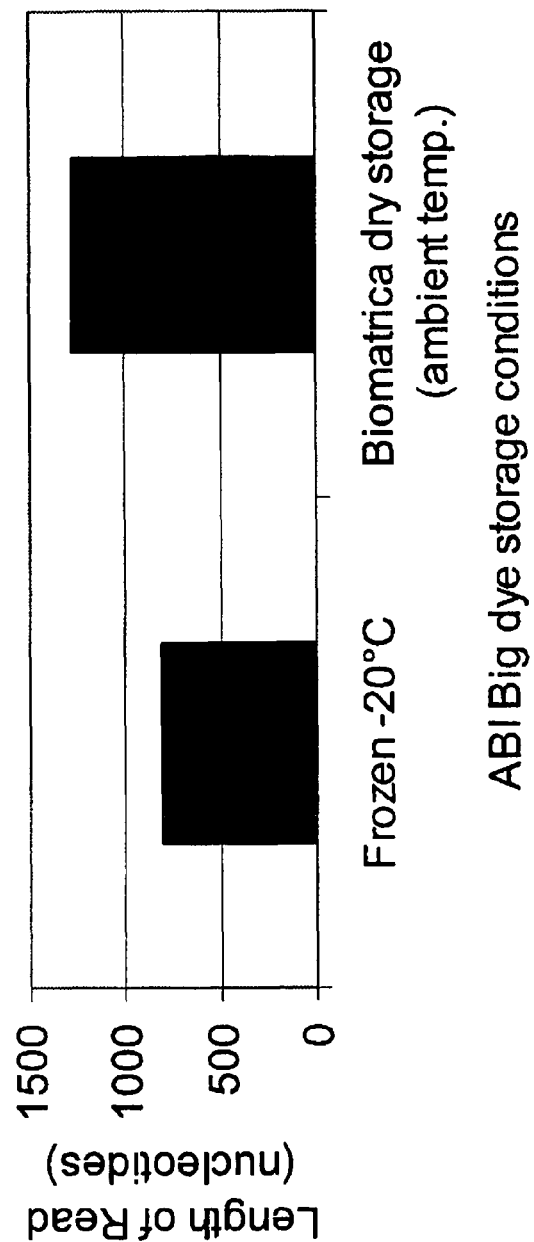
FIG. 15 shows (A) length of read (number of bases) for PCR reaction products amplified using Big Dye™ enzyme stored frozen, and stored dry on a dissolvable matrix at ambient temperature; and (B) cycle sequencing results.
Figure 15B:
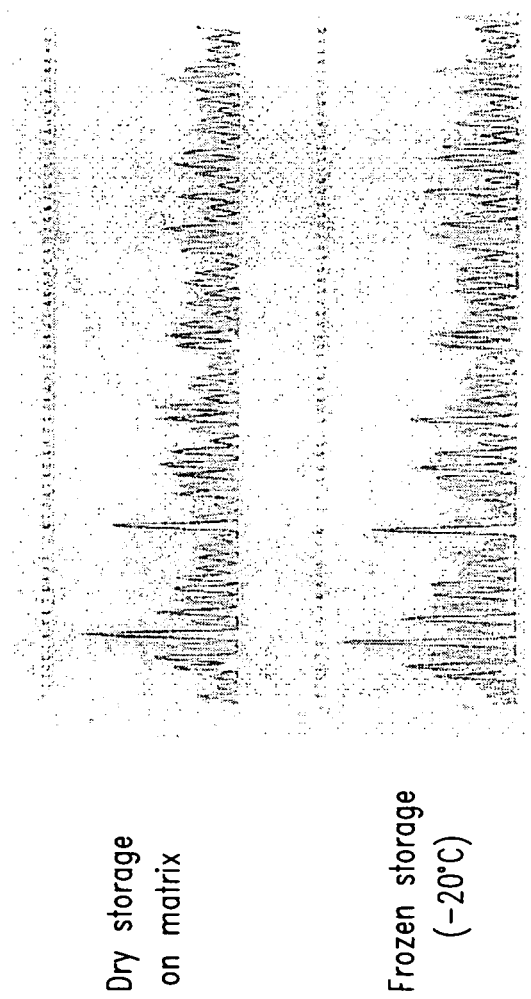
Figure 16:
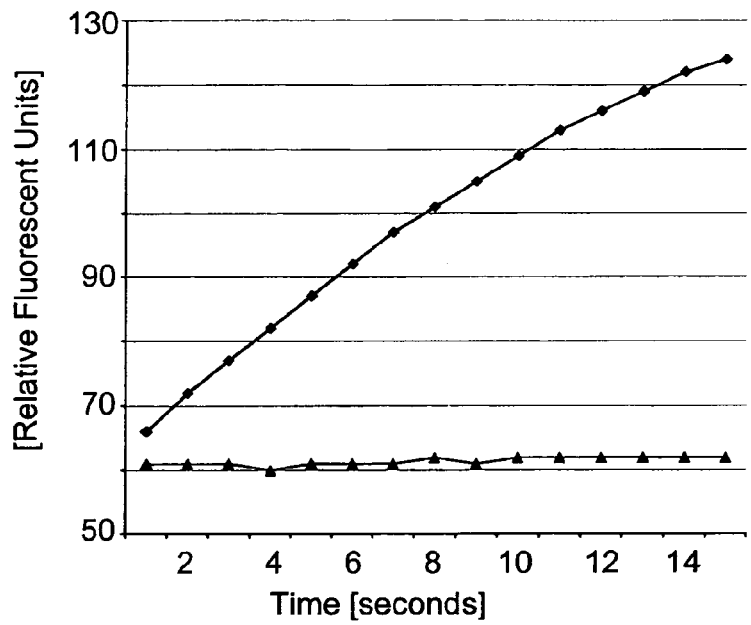
FIG. 16 shows HIV protease kinetics after dry storage on a dissolvable matrix.

Fresh, appropriately stored, active Big Dye™ (ABI) was applied to the dissolvable PVA matrix in 1× reaction buffer in the presence of 5% final concentration of trehalose (Fluka #90210). To test if the Big Dye™ enzyme can be dehydrated in the presence of plasmid and sequencing primers without loss of activity, Big Dye™ was spotted in the presence of M13 forward primer and puc19. The concentration per well in a 96 well plate was equivalent to the concentration of frozen stored Sequenase™ (USB) used for one sequencing reaction. Control Sequenase™ was stored in the conventional in a −20° C. freezer. The complete well was hydrated with 20 µl of 1× reaction buffer for 30 minutes. PCR reactions were performed according to the suppliers' recommendations for 35 cycles. The PCR products of the cycle sequencing reaction were purified and analyzed using an ABI capillary sequencing instrument according to the manufacturer's instructions. The sequences of the frozen and the dry-stored Big Dye™ as well as the dried Big Dye™ in the presence and absence of the plasmid and sequencing primers were compared using Mac Vector sequence analysis programs. The sequence quality was identical, in the first 700 bases. Longer reads were obtained using the dried Big Dye reagents, as shown in FIG. 15.

D. Proteases

Proteases are major drug targets. Currently, proteases are used for small molecule screens to develop new drugs against viral diseases such as HIV. Protease assays are often difficult to perform because protease activity is a delicate enzymatic reaction where baseline activity of the stored protease has to be adjusted prior to each assay. The kinetics of the reaction varies based on changes in protease activity after each freeze-thaw. This section demonstrates how dried proteases in the presence of dissolvable matrix were protected from the loss of activity and could be activated after re-hydration without changes in the activity profile, resulting in a tremendous time savings for any use of the enzyme, such as for a small molecule screening project.

1) HIV Protease—HIV protease was spotted at 25 nM concentration per well of a 96 well plate pretreated with dissolvable PVA matrix in the presence of activity buffer (0.5M MES, 25% Glycerol, 1M NaCl, pH5.25) containing trehalose or validamycin A at a final concentration of 2.5-10% (w/v). As a control HIV protease was spotted in wells of polypropylene plates in the presence of trehalose or validamycin without the presence of PVA matrix. The dried HIV protease was recovered in 1×Activity buffer in the presence of 150 mM Guanidine Hydrochloride. Complete recovery was achieved one hour post rehydration. Enzymatic reaction activity was followed in a kinetic study using a fluorogenic peptide containing two fluorescent molecules in a FRET assay over a 20 minute time course. The reaction was analyzed on a Packard Fusion microtiter plate fluorometer according to the manufacturer's instructions.

No enzyme activity could be restored using the HIV protease that had been spotted with trehalose or validamycin A alone, in the absence of the dissolvable PVA matrix. By contrast, 100% of HIV protease activity was recovered using enzyme that had been spotted on the PVA matrix in the presence of trehalose and 70% of the activity was recovered from enzyme that had been dried using dissolvable matrix alone (PVA) without additional stabilizing agents.

2) FIV Protease—FIV (Feline Immunodeficiency Virus) is a lentivirus closely related to HIV. The FIV protease was spotted onto wells pretreated with dried dissolvable matrix at a concentration of 0.5 µg per well in the presence and absence of the peptide based inhibitor, TL-3 (Lee et al., 1998 PNAS 95:939). The wells containing the matrix, the protease and the inhibitor TL-3 were completely dried and stored at room temperature. The dried HIV protease was rehydrated for one hour in 1×activity buffer in the presence of 150 mM Guanidine Hydrochloride. The enzymatic reaction activity was followed in a kinetic study using a fluorogenic peptide containing two fluorescent molecules in a FRET assay over a 20 minute time course. The reaction was analyzed on a Packard Fusion microtiter plate fluorometer. The FIV protease activity was fully restored after the rehydration process and the enzymatic activity was blocked by TL-3 demonstrating that the protease and its inhibitor are fully active after dry storage at ambient temperature.

Figure 17:
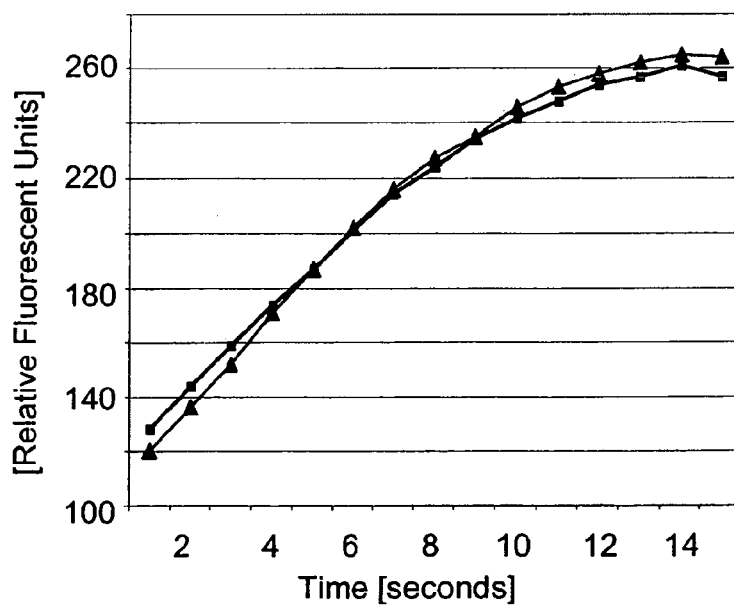
FIG. 17 shows FIV protease activity after dry storage on a dissolvable matrix.

Trehalose and validamycin were also compared as described above but for their affects on FIV protease in protease assays for the protection of enzyme activity during longterm dry matrix storage of the protease at ambient temperature on the dissolvable storage matrix. Either additive protectively stabilized the enzyme and no difference was detectable for the protection of the enzyme (FIG. 17).

E. LIGASES-T4 DNA ligase (New England Biolabs, Beverly, Mass., # M0202L) (400 U) per well was applied to the dissolvable PVA matrix prepared as described above in 1× ligation buffer in the presence of 5% final concentration of validamycin A. Control ligase was stored in a −20° C. freezer. The complete well was hydrated with 20 µl of 1× ligation buffer for 5-45 minutes. 50 ng of SalI digested, calf intestinal phosphatase dephosphorylated puc19 plasmid was ligated overnight with the rehydrated ligase in parallel with frozen stored ligase. One half of the ligation reaction was transformed into DH5alpha competent bacterial cells. The cells were plated on LB agar plates and the transformation rate was analyzed by colony counts. Only religated plasmids could form colonies under these conditions. The dry stored ligase had 5-fold higher colony counts than the frozen stored ligase.

F. Reconstitutable HIV protease Assay—Currently HIV protease assays require defrosting the protease, resuspension in an activity buffer, resuspension of the fluorogenic substrate in its buffer system, mixing of the solution and application of the mixture onto special fluorescent 96-well plates for a pre-test of the defrosted enzyme activity. After determination of the protease activity, the assay for the screening of inhibitory compounds can begin and is usually conducted in 96 well format. The same procedure has to be repeated involving the pipetting steps described above. This section shows how using the protease supplied according to the compositions and methods of the present application on the dissolvable matrix in dried form, no pretest has to be performed, since the HIV protease activity remained stable under dried conditions.

Figure 18:
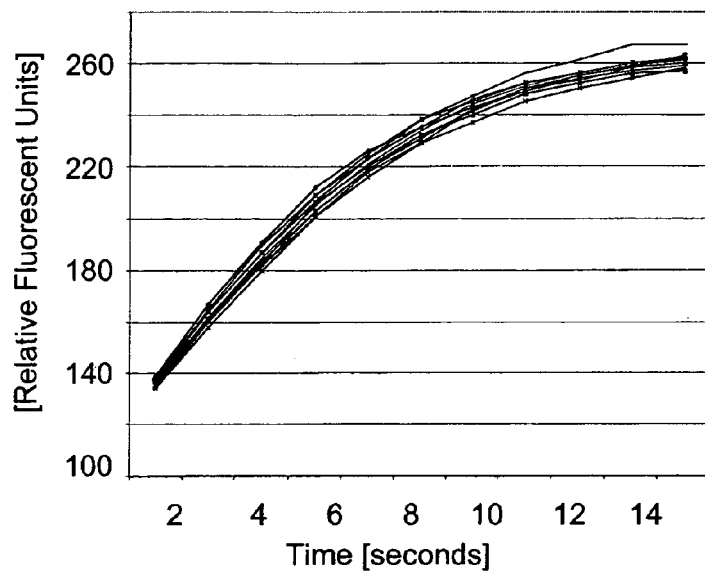
FIG. 18 shows HIV protease activity after dry storage.

Using the dissolvable PVA matrix prepared as described above, HIV protease and FIV protease were spotted and dried in their respective activity buffer at the appropriate reaction concentration. The fluorogenic protease substrate and the negative control well containing the protease inhibitor were supplied in their buffer in dried form on 96 well plates as well. The operator of the screen had only to add water alone or containing a test inhibitor screening compound to rehydrate the protease containing well, and water to the fluorescent substrate well. Accordingly, for rehydrating some FIV protease wells the TL-3 inhibitor described above was included. The handling time for the assay was reduced by more than 10 fold, and representative results are shown in FIG. 18. Similar time savings can be obtained for other biochemical assays, screens or experimental protocols.

Example 5

Longterm Storage of Cells Using the Dissolvable PVA Matrix

This example describes longterm dry storage at ambient temperature of *E. coli* cells on a dissolvable matrix material.

Figure 19:
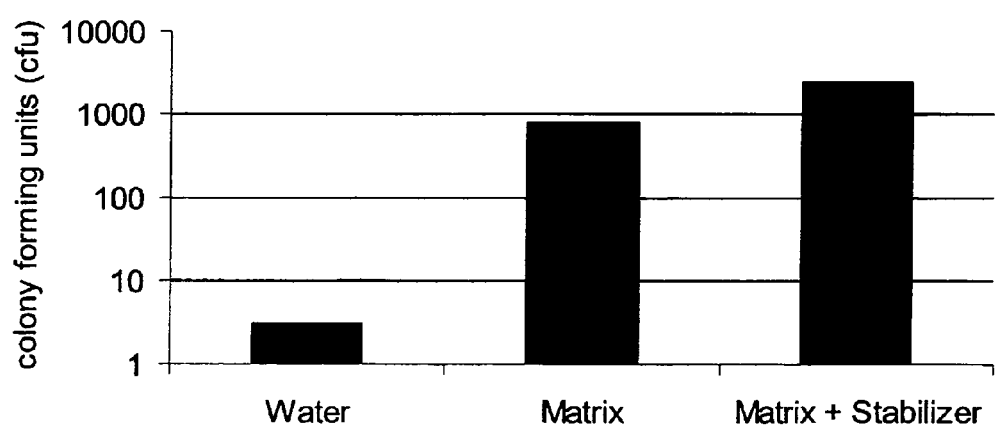
FIG. 19 shows *E. Coli* transformation rate after dry storage on a dissolvable matrix.

Equal numbers of *Escherichia coli* (DH5 alpha) bacteria were resuspended in LB growth media and spotted in wells of a 96 well plate: a) without dissolvable matrix in growth medium, b) with dried dissolvable PVA matrix and c) mixed with 5% validamycin A and spotted on dried dissolvable matrix. The plates were dried overnight and stored at ambient temperature. The wells with the three different conditions were hydrated with growth media for one hour and the content of the wells were plated onto bacterial culture LB plates. The plates were incubated at 37° C. overnight. The *E. coli* recovery rate was analyzed through counting of the bacterial colonies, as shown in FIG. 19.

The dissolvable matrix is also prepared and used for the dried long-term storage of cells, including other bacteria, plant, animal or human cells, and for dry storage of phages, viruses (e.g., lentivirus, baculovirus, etc.).

Embodiments of the dry matrix storage compositions and methods of the invention are also contemplated for use with antibodies, RNA, enzymes, and other biological samples as provided herein.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A biological sample storage device for dry storage of one or a plurality of biological samples without refrigeration and lyophilization, comprising a sample plate comprising one or a plurality of sample wells for containing a biological sample, wherein one or more of said wells comprises a matrix material that dissolves in water; wherein the matrix comprises at least one stabilizer, wherein if the at least one stabilizer comprises a first stabilizer that is trehalose, then a trehalase inhibitor is also present as a second stabilizer; wherein the matrix is free of fibers and cellulosic materials; and wherein at least 50% of the biological sample is recovered from the matrix when a solvent is added to the matrix when the matrix has the biological sample stored therein without refrigeration and without lyophilization.

2. The biological sample storage device according to claim 1 which comprises a lid; and a closure means for closing the lid onto the sample plate.

3. The biological sample storage device of claim 2 wherein the closure means comprises a magnetic closure.

4. The biological sample storage device according to claim 2 which comprises an airtight closure joint.

5. The biological sample storage device according to claim 4 comprising an airtight closure joint around each well.

6. The biological sample storage device according to claim 3 comprising an airtight closure joint around each well.

7. The biological sample storage device of claim 1 wherein the inhibitor is selected from the group consisting of validamycin A, TL-3, sodium orthovanadate, sodium fluoride, N-α-tosyl-Phe-chloromethylketone, N-α-tosyl-Lys-chloromethylketone, aprotinin, phenyhnethylsulfony fluoride and diisopropylfluoro-phosphate.

8. The biological sample storage device of claim 1 wherein the inhibitor is selected from the group consisting of a kinase inhibitor, a phosphatase inhibitor, a caspase inhibitor, a granzyme inhibitor, a cell adhesion inhibitor, a cell division inhibitor, a cell cycle inhibitor, a lipid signaling inhibitor and a protease inhibitor.

9. The biological sample storage device of claim 1 wherein the inhibitor is selected from the group consisting of a reducing agent, an alkylating agent and an antimicrobial agent.

10. The biological sample storage device according to claim 1 wherein the matrix material comprises polyvinyl alcohol.

11. The biological sample storage device according to claim 1 wherein the matrix material comprises hydroxyectoine.

12. A composition comprising (i) a matrix material that dissolves in water; wherein the matrix comprises at least one stabilizer, wherein if the at least one stabilizer comprises a first stabilizer that is trehalose, then a trehalase inhibitor is also present as a second stabilizer; wherein the matrix is free of fibers and cellulosic materials and (ii) a biological sample stored in the matrix without refrigeration and without lyophilization wherein at least 50% of the biological sample stored in the matrix is recovered from the matrix when a solvent is added to the matrix.

* * * * *